(12) United States Patent
Dolle et al.

(10) Patent No.: US 7,767,814 B2
(45) Date of Patent: Aug. 3, 2010

(54) SUBSTITUTED PIPERIDINE COMPOUNDS AND METHODS OF THEIR USE

(75) Inventors: Roland Ellwood Dolle, King of Prussia, PA (US); Bertrand Le Bourdonnec, East Fallowfield Township, PA (US)

(73) Assignee: Adolor Corporation, Exton, PA (US)

( * ) Notice: Subject to any disclaimer, the term of this patent is extended or adjusted under 35 U.S.C. 154(b) by 825 days.

(21) Appl. No.: 11/442,075

(22) Filed: May 25, 2006

(65) Prior Publication Data
US 2006/0223840 A1    Oct. 5, 2006

Related U.S. Application Data

(62) Division of application No. 10/798,664, filed on Mar. 11, 2004, now Pat. No. 7,087,749.

(51) Int. Cl.
C07D 221/22    (2006.01)
C07D 221/02    (2006.01)
A01N 43/42    (2006.01)

(52) U.S. Cl. .......................... 546/79; 546/112; 514/290
(58) Field of Classification Search ................. 546/112, 546/79
See application file for complete search history.

(56) References Cited

U.S. PATENT DOCUMENTS

| | | | |
|---|---|---|---|
| 4,176,186 A | 11/1979 | Goldberg et al. | 424/260 |
| 4,987,126 A | 1/1991 | Bargiotti et al. | 514/34 |
| 5,159,081 A | 10/1992 | Cantrell et al. | 546/226 |
| 5,250,542 A | 10/1993 | Cantrell et al. | 514/315 |
| 5,270,323 A | 12/1993 | Milne, Jr. et al. | 514/309 |
| 5,434,171 A | 7/1995 | Frank et al. | 514/331 |
| 5,731,322 A | 3/1998 | Dondio et al. | 514/292 |
| 5,972,954 A | 10/1999 | Foss et al. | 514/292 |
| 6,531,481 B2 * | 3/2003 | Carroll et al. | 514/299 |
| 6,552,032 B2 * | 4/2003 | Carroll et al. | 514/290 |
| 6,593,348 B2 * | 7/2003 | Carroll et al. | 514/331 |
| 6,900,228 B1 * | 5/2005 | Carroll et al. | 514/329 |

FOREIGN PATENT DOCUMENTS

WO    99/45925    9/1999

OTHER PUBLICATIONS

Aceto, *Chemical Abstracts* abstract 125:185593, 1996.
Bagnol, D., et al., "Cellular localization and distribution of the cloned mu and kappa opioid receptors in rat gastrointestinal tract," *Neuroscience*, 1997, 81(2), 579-591.
Bagnol, D., et al., "Changes in enkephalin immunoreactivity of sympathetic ganglia and digestive tract of the cat after splanchnic nerve ligation," *Regul. Peptides*, 1993, 47, 259-273.
Bhargava, H.N., et al., "Effect of nitric oxide synthase inhibition on tolerance to the analgesic action of D-Pen$^2$, D-Pen$^5$ enkephalin and morphine in the mouse," *Neuropeptides*, 1996, 30(3), 219-223.
Bilsky, E.J., "Effects of naloxone and D-phe-cys-tyr-D-trp-arg-thr-pen-thr-NH$_2$ and the protein kinase inhibitors H7 and H8 on acute morphine dependence and antinociceptive tolerance in mice," *J. Pharmacol. Exp. Ther.*, 1996, 277, 484-490.
Buschmann, H., et al., Verlag GMbH & Co. KgaA, Weinheim, 2002.
Dorland's Illustrated Medical Dictionary, 27$^{th}$ Ed., W.B. Saunders Co., Phila., PA, 1988, p. 816.
Dorland's Illustrated Medical Dictionary, 27$^{th}$ Ed., W.B. Saunders Co., Phila., PA, 1988, p. 375.
Dourish, C.T., et al., "Enhancement of morphine analgesia and prevention of morphine tolerance in the rat by the cholecystokinin antagonist L-364, 718," *Eur. J. Pharmacol.*, 1988, 147, 469-472.
Drewes, S.E., et al., "Synthesis, resolution and assignment of absolute configuration of 2-(α-hydroxy)aryl acrylate esters," *Tetrah.: Asymmetry*, 1992, 3(2), 255-260.
Greene, T.W., et al., Protective Groups in Organic Synthesis, 3$^{rd}$ Ed., Wiley & Sons, 1991.
Jacobson, *Chemical Abstracts* abstract 125:185591, 1995.
Jain, K.K., "A guide to drug evaluation for chronic pain," *Emerging Drugs*, 2000, 5(2), 241-257.
Koch, T.R., et al., "Inhibitory neuropeptides and intrinsic inhibitory innervation of descending human colon," *Digestive Diseases & Sciences*, 1991, 36(6), 712-718.
Kreek, M.-J., et al., "Naloxone, a specific opioid antagonist, reverses chronic idiopathic constipation," *J. Lancet*, 1983, 261-262.
Livingston, E.H., et al., "Postoperative ileus," *Digestive Diseases and Sciences*, 1990, 35(1), 121-132.
Mack, D.J., "Paralytic ileus: response to naloxone," *Br. J. Surg.*, 1989, 76(10), p. 1101.
Mao, M.J., et al., "Oral administration of dextromethorphan prevents the development of morphine tolerance and dependence in rats," *Pain*, 1996, 67, 361-368.
Nichols, M.L., et al., "Enhancement of the antiallodynic and antinociceptive efficacy of spinal morphine by antisera to dynorphin A (1-13) or MK-801 in a nerve-ligation model of peripheral neuropathy," *Pain*, 1997, 69, 317-322.
Perlmutter, P., et al., "A simple route to α-substituted-β-amino ester precursors of carbapenem antibiotics," *J. Org. Chem.*, 1995, 60, 6515-6522.
Perlmutter, P., et al., "Diastereoselection in the nucleophilic conjugate addition of amines to 2-hydroxyalkylpropenoates," *Tetrah. Lett.*, 1988, 29(8), 949-952.
Physician's Desk Reference, 1999.

(Continued)

*Primary Examiner*—D. Margaret Seaman
*Assistant Examiner*—Nizal S Chandrakumar
(74) *Attorney, Agent, or Firm*—Feldman Gale, P.A.; David A. Cherry

(57) ABSTRACT

Certain 4-aryl-piperidine compounds, including N-substituted 9β-substituted-5-(3-substituted-phenyl)morphans and N-substituted octahydro-4a-(3-hydroxyphenyl)-10a-methylbenzo[g]isoquinolines, pharmaceutical compositions, and methods of their use, inter alia, as opioid antagonists are disclosed.

62 Claims, No Drawings

OTHER PUBLICATIONS

Reisine, T., et al., "Opioid analgesics and antagonists," *Goodman & Gilman's The Pharmacological Basis of Therapeutics*, 9$^{th}$ Ed., 1996, Chapter 23, 521-555.

Remington's Pharmaceutical Sciences, *Mack Pub. Co.*, Easton, PA, 1980.

Resnick, J., et al., "Delayed gastric emptying and postoperative Ileus after nongastric abdominal surgery: Part I," *Am. J. of Gastroenterology*, 1997, 92(5), 751-762.

Resnick, J., et al., "Delayed gastric emptying and postoperative ileus after nongastric abdominal surgery: Part II," *Am. J. of Gastroenterology*, 1997, 92(6), 934-940.

Schang, J.C., et al., "Beneficial effects of naloxone in a patient with intestinal pseudoobstruction," *Am. J. Gastroenerol*, 1985, 80(6), 407-411.

Schuller, A.G.P., et al., "M6G, but not morphine, inhibits GI transit in MU opioid receptor deficient mice," Abstract No. 210.7, *Society of Neurosc.*, 1998, 24, p. 524.

Shaw, W.N., et al., "Effect of phenylpiperidine opioid antagonists on food consumption and weight gain of the obese zucker rat," *J. Pharm. & Exp. Ther.*, 1990, 253(1), 85-89.

Thomas, J.B., et al., "N-substituted 9β-methyl-5-(-3hydroxyphenyl)morphans are opioid receptor pure antagonists," *J. Med. Chem.*, 1998, 41, 4143-4149.

Thomas, J.B., et al., "N-substituted octahydro-4a-(3-hydroxyphenyl)-10a-methyl-benzo[g]isoquinolines are opioid receptor pure antagonists," *Bioorganic & Medicinal Chem. Letts.*, 1998, 8, 3149-3152.

Thomas, *Tetrahedron Letters*, vol. 40, pp. 403-406, 1999.

Werner, J.A., et al., "Synthesis of *trans*-3,4-dimethyl-4-(3-hydroxyphenyl)piperidine opioid antagonists: application of the *Cis*-thermal elimination of carbonates to alkaloid synthesis," *J. Org. Chem.*, 1996, 61(2), 587-597.

Wittert, G., et al., "Tissue distribution of opioid receptor gene expression in the rat," *Biochem & Biophys. Res. Commun.*, 1996, 218(3), 877-881.

Zimmerman, D.J., et al., "Discovery of a potent, peripherally selective *trans*-3,4-dimethyl-4-(3-hydroxyphenyl) piperidine opioid antagonist for the treatment of gastrointestinal motility disorders," *J. Med. Chem.*, 1994, 37(15), 2262-2265.

* cited by examiner

SUBSTITUTED PIPERIDINE COMPOUNDS AND METHODS OF THEIR USE

CROSS REFERENCE TO RELATED APPLICATIONS

This application is a divisional of U.S. patent application Ser. No. 10/798,664, filed Mar. 11, 2004, now U.S. Pat. No. 7,087,749, the entire disclosure of which is incorporated by reference.

FIELD OF THE INVENTION

The invention relates to 4-aryl-piperidine derivatives, including N-substituted 9β-substituted-5-(3-substituted-phenyl)morphans and N-substituted octahydro-4a-(3-hydroxyphenyl)-10a-methyl-benzo[g]isoquinolines, pharmaceutical compositions containing these compounds, and methods of their use.

BACKGROUND OF THE INVENTION

It is well known that opioid drugs target three types of endogenous opioid receptors (i.e., μ, δ, and κ receptors) in biological systems. Many opiates, such as morphine, are μ opioid agonists that are often used as analgesics for the treatment of severe pain due to their activation of μ opioid receptors in the brain and central nervous system (CNS). Opioid receptors are, however, not limited to the CNS, and may be found in other tissues throughout the body, i.e., peripheral to the CNS. A number of side effects of opioid drugs may be caused by activation of these peripheral receptors. For example, administration of μ opioid agonists often results in intestinal dysfunction due to the large number of receptors in the wall of the gut (Wittert, G., Hope, P. and Pyle, D., *Biochemical and Biophysical Research Communications*, 1996, 218, 877-881; Bagnol, D., Mansour, A., Akil, A. and Watson, S. J., *Neuroscience*, 1997, 81, 579-591). Specifically, opioids are generally known to cause nausea and vomiting, as well as inhibition of normal propulsive gastrointestinal function in animals and man (Reisine, T., and Pasternak, G., *Goodman & Gilman's The Pharmacological Basis of Therapeutics, Ninth Edition*, 1996, 521-555), resulting in side effects such as, for example, constipation.

Recent evidence has indicated that naturally-occurring endogenous opioid compounds may also affect propulsive activity in the gastrointestinal (GI) tract. Met-enkephalin, which activates μ and δ receptors in both the brain and gut, is one of several neuropeptides found in the GI tract (Koch, T. R., Carney, J. A., Go, V. L., and Szurszewski, J. H., *Digestive Diseases and Sciences*, 1991, 36, 712-728). Additionally, receptor knockout techniques have shown that mice lacking μ opioid receptors may have faster GI transit times than wild-type mice, suggesting that endogenous opioid peptides may tonically inhibit GI transit in normal mice (Schuller, A. G. P., King, M., Sherwood, A. C., Pintar, J. E., and Pasternak, G. W., *Society of Neuroscience Abstracts* 1998, 24, 524). Studies have shown that opioid peptides and receptors located throughout the GI tract may be involved in normal regulation of intestinal motility and mucosal transport of fluids in both animals and man (Reisine, T., and Pasternak, G., Goodman & Gilman's *The Pharmacological Basis of Therapeutics, Ninth Edition*, 1996, 521-555). Other studies show that the sympathetic nervous system may be associated with endogenous opioids and control of intestinal motility (Bagnol, D., Herbrecht, F., Jule, Y., Jarry, T., and Cupo, A., *Regul. Pept.*, 1993, 47, 259-273). The presence of endogenous opioid compounds associated with the GI tract suggests that an abnormal physiological level of these compounds may lead to bowel dysfunction.

It is a common problem for patients having undergone surgical procedures, especially surgery of the abdomen, to suffer from a particular bowel dysfunction called post-surgical (or post-operative) ileus. "Ileus," as used herein, refers to the obstruction of the bowel or gut, especially the colon. See, e.g., *Dorland's Illustrated Medical Dictionary*, 27th ed., page 816, (W.B. Saunders Company, Philadelphia, Pa., 1988). Ileus should be distinguished from constipation, which refers to infrequency of or difficulty in feces evacuation. See, e.g., *Dorland's Illustrated Medical Dictionary*, 27th ed., page 375, (W. B. Saunders Company, Philadelphia, 1988). Ileus may be diagnosed by the disruption of normal coordinated movements of the gut, resulting in failure of intestinal contents propulsion. See, e.g., Resnick, J., *Am. J. of Gastroenterology*, 1997, 92, 751 and Resnick, J. *Am. J. of Gastroenterology*, 1997, 92, 934. In some instances, particularly following surgery, including surgery of the abdomen, the bowel dysfunction may become quite severe, lasting for more than a week and affecting more than one portion of the GI tract. This condition is often referred to as post-surgical (or post-operative) paralytic ileus and most frequently occurs after laparotomy (see Livingston, E. H. and Passaro, Jr., E. D., *Digestive Diseases and Sciences*, 1990, 35, 121). Similarly, post-partum ileus is a common problem for women in the period following childbirth, and is thought to be caused by similar fluctuations in natural opioid levels as a result of birthing stress.

Gastrointestinal dysmotility associated with post-surgical ileus is generally most severe in the colon and typically lasts for 3 to 5 days. The administration of opioid analgesics to a patient after surgery may often contribute to bowel dysfunction, thereby delaying recovery of normal bowel function. Since virtually all patients receive opioid analgesics, such as morphine or other narcotics, for pain relief after surgery, particularly major surgery, current post-surgical pain treatment may actually slow recovery of normal bowel function, resulting in a delay in hospital discharge and increasing the cost of medical care.

Post-surgical and post-partum ileus may also occur in the absence of exogenous opioid agonists. It would be of benefit to inhibit the natural activity of endogenous opioids during and/or after periods of biological stress, such as surgery and childbirth, so that ileus and related forms of bowel dysfunction can be prevented and/or treated. Currently, therapies for ileus include functional stimulation of the intestinal tract, stool softeners, laxatives, lubricants, intravenous hydration, and nasogastric decompression. These prior art methods suffer from drawbacks, for example, as lacking specificity for post-surgical or post-partum ileus. And these prior art methods offer no means for prevention. If ileus could be prevented, hospital stays, recovery times, and medical costs would be significantly decreased, in addition to the benefit of minimizing patient discomfort. Thus, drugs that selectively act on opioid receptors in the gut would be ideal candidates for preventing and/or treating post-surgical and post-partum ileus. Of those, drugs that do not interfere with the effects of opioid analgesics in the CNS would be of special benefit in that they could be administered simultaneously for pain management with limited side effects.

Peripheral opioid antagonists that do not cross the blood-brain barrier into the CNS are known in the literature and have been tested in relation to their activity on the GI tract. In U.S. Pat. No. 5,250,542, U.S. Pat. No. 5,434,171, U.S. Pat. No. 5,159,081, and U.S. Pat. No. 5,270,328, peripherally selective piperidine-N-alkylcarboxylate opioid antagonists are described as being useful in the treatment of idiopathic constipation, irritable bowel syndrome, and opioid-induced constipation. In addition, U.S. Pat. No. 4,176,186 describes quaternary derivatives of noroxymorphone (i.e., methylnaltrexone) that are said to prevent or relieve the intestinal immobility side effect of narcotic analgesics without reducing analgesic effectiveness. U.S. Pat. No. 5,972,954 describes the use of methylnaltrexone, enteric-coated methylnaltrexone, or other quaternary derivatives of noroxymorphone for preventing and/or treating opioid- and/or non-opioid-induced side effects associated with opioid administration.

General opioid antagonists, such as naloxone and naltrexone, have also been implicated as being useful in the treatment of GI tract dysmotility. For example, U.S. Pat. No. 4,987,126 and Kreek, M. J., Schaefer, R. A., Hahn, E. F., Fishman, *J. Lancet*, 1983, 1, 8319, 261 disclose naloxone and other morphinan-based opioid antagonists (i.e., naloxone, naltrexone) for the treatment of idiopathic gastrointestinal dysmotility. In addition, naloxone has been shown to effectively treat non-opioid induced bowel obstruction, implying that the drug may act directly on the GI tract or in the brain (Schang, J. C., Devroede, G., *Am. J. Gastroenerol.*, 1985, 80, 6, 407). Furthermore, it has been implicated that naloxone may provide therapy for paralytic ileus (Mack, D. J. Fulton, J. D., *Br. J. Surg.*, 1989, 76, 10, 1101). However, it is well known that activity of naloxone and related drugs is not limited to peripheral systems and may interfere with the analgesic effects of opioid narcotics.

Alvimopan is an orally active, gastrointestinal (GI) restricted μ opioid antagonist being developed to alleviate the GI side effects associated with narcotic therapy. Alvimopan inhibits [$^3$H]diprenorphine binding to cloned human opioid receptors with $K_i$ values of 0.44 nM, 10 nM and 92 nM for μ, δ and κ receptors respectively. This compound differs from previously characterized peripherally selective opioid antagonists by its potency and degree of peripheral receptor selectivity [Zimmerman, et al., *J. Med. Chem.*, 1994, 37, 2262-2265].

The μ opioid antagonist family of trans-3,4-Dimethyl-4-phenylpiperidines has been indicated as food consumption reducing agents [W. N. Shaw, et al., *J. Pharm. and Exp. Ther.*, 1990, 253(1), 85-89]. Long-term chronic administration significantly reduced food consumption in obese test animals for as long as a phenylpiperidine μ opioid antagonist was administered, resulting in a significant decrease in weight gain compared to control. Accordingly, compounds with μ opioid antagonist properties are likely to have benefit in the treatment or management of obesity in patients, especially those non-zwitterionic compounds that would be able to cross the blood-brain barrier.

Inasmuch as post-surgical and post-partum ileus, for example, are common illnesses that add to the cost of health care and as yet have no specific treatment, there is a need for a specific and effective remedy. The majority of currently known opioid antagonist therapies is not peripherally selective and has the potential for undesirable side effects resulting from penetration into the CNS. Given the estimated 21 million inpatient surgeries and 26 million outpatient surgeries each year, and an estimate of 4.7 million patients experiencing post-surgical ileus, methods involving opioid antagonists that are not only specific for peripheral systems, but also specific for the gut, are desirable for treating post-surgical and post-partum ileus.

There is still an unfulfilled need for compounds that may be used in methods to antagonize opioid receptors, particularly where undesirable symptoms or conditions are side effects of administering exogenous opioids. The present invention is directed to these, as well as other important ends.

SUMMARY OF THE INVENTION

The present invention is generally directed to 4-aryl-piperidine derivatives, pharmaceutical compositions containing these compounds, and methods of their pharmaceutical use.

In one embodiment, the invention is directed to pharmaceutically active compounds of formula I:

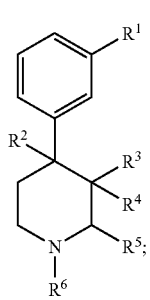

I wherein:
$R^1$ is —$OR^7$, —$NR^7R^8$, —$COOR^7$, —$CONR^7R^8$, or —$CH_2OH$;

each $R^7$ is independently H, alkyl, cycloalkyl, alkylcycloalkyl, or aralkyl;

each $R^8$ is independently H, alkyl, aralkyl, or aryl;

$R^2$, $R^3$, $R^4$, and $R^5$ are selected such that:

$R^2$ and $R^5$ together form —$(CH_2)_q$—, where q is 2 to 4, $R^3$ is alkyl, and $R^4$ is H; or $R^2$ and $R^3$ together with the carbon atoms to which they are attached form a fused carbocycle, $R^4$ is alkyl, and $R^5$ is H;

$R^6$ is H or —$(CHR^9)_mW$;

each $R^9$ is independently H, alkyl, cycloalkyl, alkylcycloalkyl, aryl, aralkyl or heteroaryl;

W is H, alkyl, cycloalkyl, alkylcycloalkyl, heterocycloalkyl, alkylheterocycloalkyl, aryl, heteroaryl, —$CH_2OH$, —$CH_2OR^7$, or —$C(=O)R^{10}$;

$R^{10}$ is —$OR^7$ or —$NR^7R^{11}$;

$R^{11}$ is H, alkyl, aralkyl, aryl or —$(CHR^9)_nC(=O)R^{12}$;

$R^{12}$ is —$OR^7$ or —$NR^7R^8$;

m is an integer from 1 to 4; and n is an integer from 1 to 4;

provided that when $R^1$ is —OH, then W is heterocycloalkyl, alkylheterocycloalkyl, —$CH_2OH$, or —$C(=O)R^{10}$; and when $R^1$ is —OH and W is heterocycloalkyl or alkylheterocycloalkyl in which the heterocyclic ring moiety of the heterocycloalkyl or alkylheterocycloalkyl contains only one heteroatom, wherein the heteroatom is nitrogen, then the heterocyclic ring moiety is connected to —$(CHR^9)_m$— through a heterocyclic ring carbon atom;

or a stereoisomer, prodrug, pharmaceutically acceptable salt, hydrate, solvate, acid hydrate, N-oxide or isomorphic crystalline form thereof.

In another embodiment, the invention is directed to pharmaceutical compositions comprising:
a pharmaceutically acceptable carrier; and
an effective amount of a compound of formula I.

In yet another embodiment, the invention is directed to methods for binding opioid receptors, in a patient in need thereof, comprising the step of:

administering to the patient a composition comprising an effective amount of a compound of formula I.

In other embodiments, the invention is directed to methods of preventing or treating gastrointestinal dysfunction, comprising the step of:

administering to a patient in need thereof, a composition comprising an effective amount of a compound of formula I.

In yet other embodiments, the invention is directed to methods of preventing or treating ileus, comprising the step of:

administering to a patient in need thereof, a composition comprising an effective amount of a compound of formula I.

In yet other embodiments, the invention is directed to methods of preventing or treating obesity, comprising the step of:

administering to a patient in need thereof, a composition comprising an effective amount of a compound a compound of formula I.

In another embodiment, the invention is directed to methods of preventing or treating a side effect associated with an opioid, comprising the step of:

administering to a patient in need thereof, a composition comprising an effective amount of a compound of formula I.

In yet another embodiment, the invention is directed to methods of preventing or treating pain, comprising the step of:

administering to a patient in need thereof, a composition, comprising:

an effective amount of an opioid; and an effective amount of a compound of formula I.

DETAILED DESCRIPTION OF ILLUSTRATIVE EMBODIMENTS

The present invention is generally directed to 4-aryl-piperidine derivatives, pharmaceutical compositions containing these compounds, and methods of their pharmaceutical use.

As employed above and throughout the disclosure, the following terms, unless otherwise indicated, shall be understood to have the following meanings.

As used herein, the term "alkyl" refers to an optionally substituted, saturated straight, branched, or cyclic hydrocarbon having from about 1 to about 20 carbon atoms (and all combinations and subcombinations of ranges and specific numbers of carbon atoms therein), with from about 1 to about 8 carbon atoms, herein referred to as "lower alkyl," being preferred. Alkyl groups include, but are not limited to, methyl, ethyl, n-propyl, isopropyl, n-butyl, isobutyl, sec-butyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

As used herein, the term "cycloalkyl" refers to an optionally substituted, alkyl group having one or more rings in their structures having from about 3 to about 20 carbon atoms (and all combinations and subcombinations of ranges and specific numbers of carbon atoms therein), with from about 3 to about 10 carbon atoms being preferred. Multi-ring structures may be bridged or fused ring structures. Groups include, but are not limited to, cyclopropyl, cyclobutyl, cyclopentyl, cyclohexyl, cyclooctyl, 2-[4-isopropyl-1-methyl-7-oxa-bicyclo[2.2.1]heptanyl], 2-[1,2,3,4-tetrahydro-naphthalenyl], and adamantyl.

As used herein, the term "alkylcycloalkyl" refers to an optionally substituted ring system comprising a cycloalkyl group having one or more alkyl substituents, wherein cycloalkyl and alkyl are each as previously defined. Exemplary alkylcycloalkyl groups include 2-methylcyclohexyl, 3,3-dimethylcyclopentyl, trans-2,3-dimethylcyclooctyl, and 4-methyldecahydronaphthalenyl.

As used herein, the term "heterocycloalkyl" refers to an optionally substituted, mono-, di-, tri-, or other multicyclic aliphatic ring system that includes at least one, and preferably from 1 to about 4 sulfur, oxygen, or nitrogen heteroatom ring members. Heterocycloalkyl groups can have from about 3 to about 20 carbon atoms (and all combinations and subcombinations of ranges and specific numbers of carbon atoms therein), with from about 4 to about 10 carbons being preferred. In other preferred embodiments, the heterocycloalkyl groups have from about 4 to about 8 ring members, wherein 1 or 2 members are sulfur, oxygen, or nitrogen and the remaining members are carbon atoms. The heterocycloalkyl group may be unsaturated, and may also be fused to aromatic rings. Examples of heterocycloalkyl groups include, for example, tetrahydrofuranyl, tetrahydrothienyl, piperidinyl, pyrrolidinyl, isoxazolidinyl, isothiazolidinyl, pyrazolidinyl, oxazolidinyl, thiazolidinyl, piperazinyl, morpholinyl, piperadinyl, decahydroquinolyl, octahydrochromenyl, octahydro-cyclopenta[c]pyranyl, 1,2,3,4,-tetrahydroquinolyl, octahydro-[2]pyrindinyl, decahydro-cycloocta[c]furanyl, and imidazolidinyl.

As used herein, "fused carbocycle" is intended to mean any optionally substituted stable 7- to 13-membered bicyclic or tricyclic carbon ring system, any of which may be saturated, partially unsaturated, or aromatic. In the 6-membered aromatic portion of any fused carbocycle, one to three carbon atoms may be optionally replaced by nitrogen atoms. In fused carbocycles containing a 5-membered aromatic ring, at least one carbon in the 5-membered ring portion must be replaced with an oxygen, nitrogen, or sulfur atom, two carbons may be optionally replaced with a sulfur atom and a nitrogen atom, an oxygen atom and a nitrogen atom, or two nitrogen atoms; or three carbon atoms may be optionally replaced with three nitrogen atoms. Examples of such fused carbocycles include, but are not limited to, tetrahydroindene, tetrahydronaphthalene, 5,6,7,8,8a,9,10,10a-octahydro-2,3,6-triaza-anthracene, 4,4a,5,6,7,8,8a,9-octahydro-2H-pyrrolo[3,4-g]isoquinoline, 4,4a,5,6,7,8,8a,9-octahydro-furo[3,4-g]isoquinoline, and tetrahydro-anthracene.

As used herein, the term "alkenyl" refers to an alkyl group having from about 2 to about 10 carbon atoms and one or more double bonds (and all combinations and subcombinations of ranges and specific numbers of carbon atoms therein), wherein alkyl is as previously defined. Alkenyl groups can be optionally substituted.

As used herein, the term "alkynyl" refers to an alkyl group having from about 2 to about 10 carbon atoms and one or more triple bonds (and all combinations and subcombinations of ranges and specific numbers of carbon atoms therein), wherein alkyl is as previously defined. Alkynyl groups can be optionally substituted.

As used herein, the term "aryl" refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

As used herein, the term "aralkyl" refers to alkyl radicals bearing an aryl substituent and have from about 6 to about 50 carbon atoms (and all combinations and subcombinations of ranges and specific numbers of carbon atoms therein), with from about 6 to about 10 carbon atoms being preferred. Aralkyl groups can be optionally substituted. Non-limiting examples include, for example, benzyl, diphenylmethyl, triphenylmethyl, phenylethyl, and diphenylethyl.

As used herein, the term "alkoxyl" refers to an optionally substituted alkyl-O— group wherein alkyl is as previously defined. In some preferred embodiments, the alkyl moieties of the alkoxy groups have from about 1 to about 4 carbon atoms. Exemplary alkoxy groups include, but are not limited to, methoxy, ethoxy, n-propoxy, i-propoxy, n-butoxy, and heptoxy.

As used herein, the term "aryloxyl" refers to an optionally substituted aryl-O— group wherein aryl is as previously defined. Exemplary aryloxy groups include, but are not limited to, phenoxy and naphthoxy.

As used herein, the term "aralkoxyl" refers to an optionally substituted aralkyl-O— group wherein aralkyl is as previously defined. Exemplary aralkoxy groups include, but are not limited to, benzyloxy, 1-phenylethoxy, 2-phenylethoxy, and 3-naphthylheptoxy.

As used herein, the term "halo" refers to a fluoro, chloro, bromo, or iodo moiety attached to a compound of the invention.

As used herein, the term "heteroaryl" refers to an optionally substituted, mono-, di-, tri- or other multicyclic aromatic ring system that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl. Heteroaryl may be optionally attached via a carbon or a heteroatom to the rest of the molecule.

As used herein, the term "heteroaralkyl" refers to an optionally substituted, heteroaryl substituted alkyl radicals having from about 2 to about 50 carbon atoms (and all combinations and subcombinations of ranges and specific numbers of carbon atoms therein), with from about 6 to about 25 carbon atoms being preferred. Non-limiting examples include 2-(1H-pyrrol-3-yl)ethyl, 3-pyridylmethyl, 5-(2H-tetrazolyl)methyl, and 3-(pyrimidin-2-yl)-2-methylcyclopentanyl.

As used herein, the term "spiroalkyl" refers to an optionally substituted, alkylene diradical, both ends of which are bonded to the same carbon atom of the parent group to form a spirocyclic group. The spiroalkyl group, taken together with its parent group, as herein defined, has 3 to 20 ring atoms. Preferably, it has 3 to 10 ring atoms. Exemplary spiroalkyl groups taken together with its parent group include, but are not limited to, 1-(1-methyl-cyclopropyl)-propan-2-one, 2-(1-phenoxy-cyclopropyl)-ethylamine, and 1-methyl-spiro[4.7]dodecane.

Typically, substituted chemical moieties include one or more substituents that replace hydrogen. Exemplary substituents include, for example, halo (e.g., F, Cl, Br, I), alkyl, cycloalkyl, alkylcycloalkyl, alkenyl, alkynyl, aralkyl, aryl, heteroaryl, heteroaralkyl, spiroalkyl, heterocycloalkyl, hydroxyl (—OH), alkoxyl, aryloxyl, aralkoxyl, nitro (—NO2), cyano (—CN), amino (—NH$_2$), —N-substituted amino (—NHR"), —N,N-disubstituted amino (—N(R")R"), carboxyl (—COOH), —C(=O)R", —OR", —C(=O)OR", —C(=O)NHSO$_2$R", —NHC(=O)R", aminocarbonyl (—C(=O)NH$_2$), —N-substituted aminocarbonyl (—C(=O)NHR"), —N,N-disubstituted aminocarbonyl (—C(=O)N(R")R"), thiolato (SR"), sulfonic acid and its esters (SO$_3$R"), phosphonic acid and its mono-ester (P(=O)OR"OH) and di-esters (P(=O)OR"OR"), S(=O)$_2$R", S(=O)$_2$NH$_2$, S(=O)$_2$NHR", S(=O)$_2$NR"R", SO$_2$NHC(=O)R", NHS(=O)$_2$R", NR"S(=O)$_2$R", CF$_3$, CF$_2$CF$_3$, NHC(=O)NHR", NHC(=O)NR"R", NR"C(=O)NHR", NR"C(=O)NR"R", NR"C(=O)R" and the like. Aryl substituents may also include (CH$_2$)$_u$SO$_2$NR"(CH$_2$)$_v$, and (CH$_2$)$_u$CO$_2$NR"(CH$_2$)$_v$, where u and v are, independently, 0 to 3, where the methylene units are attached in a 1,2 arrangement yielding substituted aryls of the type:

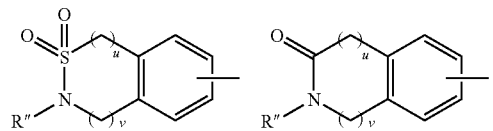

In relation to the aforementioned substituents, each moiety R" can be, independently, any of H, alkyl, cycloalkyl, alkenyl, aryl, aralkyl, heteroaryl, or heterocycloalkyl, or when (R"(R")) is attached to a nitrogen atom, R" and R" can be taken together to form a 4- to 8-membered nitrogen heterocycle, wherein the heterocycloalkyl ring is optionally interrupted by one or more additional —O—, —S—, —SO, —SO$_2$—, —NH—, —N(alkyl)-, or —N(aryl)-groups, for example.

As used herein, the term "antagonist" refers to a compound that binds to a receptor to form a complex that preferably does not elicit any response, in the same manner as an unoccupied receptor, and does not alter the equilibrium between inactive and active receptor.

As used herein, the term "prodrug" refers to compounds that may serve to maximize the amount of active species that reaches the desired site of reaction that are themselves typically inactive or minimally active for the activity desired, but through biotransformation are converted into biologically active metabolites.

As used herein, the term "stereoisomers" refers to compounds that have identical chemical constitution, but differ as regards the arrangement of the atoms or groups in space.

As used herein, the term "partial stereoisomer" refers to stereoisomers having two or more chiral centers wherein at least one of the chiral centers has defined stereochemistry (i.e., R or S) and at least one has undefined stereochemistry (i.e., R or S). When the term "partial stereoisomers thereof" is used herein, it refers to any compound within the described genus whose configuration at chiral centers with defined stereochemistry centers is maintained and the configuration of each undefined chiral center is independently selected from R or S. For example, if a stereoisomer has three chiral centers and the stereochemical configuration of the first center is defined as having "S" stereochemistry, the term "or partial stereoisomer thereof" refers to stereoisomers having SRR, SRS, SSR, or SSS configurations at the three chiral centers, and mixtures thereof.

As used herein, the term "N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

As used herein, the term "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both basic nitrogen atom and acidic groups often exist in equilibrium with their zwitterionic forms. Thus, any of the compounds described herein throughout that contain, for example, both basic nitrogen and acidic groups, also include reference to their corresponding zwitterions.

As used herein, the term "effective amount" refers to an amount of a compound as described herein that may be therapeutically effective to inhibit, prevent or treat the symptoms of particular disease, disorder or side effect. Such diseases, disorders and side effects include, but are not limited to, those pathological conditions associated with the administration of opioids (for example, in connection with the treatment and/or prevention of pain), wherein the treatment or prevention comprises, for example, inhibiting the activity thereof by contacting cells, tissues or receptors with compounds of the present invention. Thus, for example, the term "effective amount," when used in connection with opioids, for example, for the treatment of pain, refers to the treatment and/or prevention of the painful condition. The term "effective amount," when used in connection with opioid antagonist compounds, refers to the treatment and/or prevention of side effects typically associated with opioids including, for example, such side effects as constipation, nausea and/or vomiting, as well as other side effects, discussed in further detail below. The term "effective amount," when used in connection with compounds active against gastrointestinal dysfunction, refers to the treatment and/or prevention of symptoms, diseases, disorders, and conditions typically associated with gastrointestinal dysfunction. The term "effective amount," when used in connection with anti-ileus compounds, refers to the treatment and/or prevention of symptoms, diseases, disorders, and conditions typically associated with ileus.

As used herein, the term "pharmaceutically acceptable" refers to those compounds, materials, compositions, and/or dosage forms that are, within the scope of sound medical judgment, suitable for contact with the tissues of human beings and animals without excessive toxicity, irritation, allergic response, or other problems or complications commensurate with a reasonable benefit/risk ratio. The term specifically encompasses veterinary uses.

As used herein, the expressions "in combination with," "combination therapy," and "combination products" refer, in certain embodiments, to the concurrent administration to a patient of opioids, an anesthetic agent (inhaled anesthetic, hypnotic, anxiolytic, neuromuscular blocker and opioid) and/or optional ingredients (antibiotics, antivirals, antifungals, anti-inflammatories, anesthetics and mixtures thereof) and the compounds of formula I. When administered in combination, each component may be administered at the same time or sequentially in any order at different points in time. Thus, each component may be administered separately but sufficiently closely in time so as to provide the desired therapeutic effect.

As used herein, the term "dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

As used herein, the term "pain" refers to the perception or condition of unpleasant sensory or emotional experience, associated with actual or potential tissue damage or described in terms of such damage. "Pain" includes, but is not limited to, two broad categories of pain: acute and chronic pain (Buschmann, H.; Christoph, T; Friderichs, E.; Maul, C.; Sundermann, B; eds.; *Analgesics*, Wiley-VCH, Verlag GMbH & Co. KgaA, Weinheim; 2002; Jain, K. K. "A Guide to Drug Evaluation for Chronic Pain"; *Emerging Drugs,* 5(2), 241-257 (2000)). Non-limiting examples of pain include nociceptive pain, inflammatory pain, visceral pain, somatic pain, neuropathic pain, AIDS pain, cancer pain, phantom pain, and psychogenic pain, and pain resulting from hyperalgesia, pain caused by rheumatoid arthritis, migraine, allodynia and the like.

As used herein, the term "gastrointestinal dysfunction" refers collectively to maladies of the stomach, small and large intestine. Non-limiting examples of gastrointestinal dysfunction include, for example, diarrhea, nausea, emesis, post-operative emesis, opioid-induced emesis, irritable bowel syndrome, opioid-bowel dysfunction, post-operative ileus, opioid-induced ileus, colitis, decreased gastric motility, decreased gastric emptying, inhibition of small intestinal propulsion, inhibition of large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, distension, abdominal or epigastric pain and discomfort, non-ulcerogenic dyspepsia, gastritis, constipation, or delayed absorption of orally administered medications or nutritive substances.

As used herein, the term "ileus" refers to the obstruction of the bowel or gut, especially the colon. See, e.g., *Dorland's Illustrated Medical Dictionary*, p. 816, 27th ed. (W.B. Saunders Company, Philadelphia 1988). Ileus should be distinguished from constipation, which refers to infrequent or difficulty in evacuating the feces. See, e.g., *Dorland's Illustrated Medical Dictionary*, p. 375, 27th ed. (W.B. Saunders Company, Philadelphia 1988). Ileus may be diagnosed by the disruption of normal coordinated movements of the gut, resulting in failure of the propulsion of intestinal contents. See, e.g., Resnick, J. *Am. J. of Gastroenterology* 1997, 92, 751 and Resnick, J., *Am. J. of Gastroenterology,* 1997, 92, 934. In some instances, particularly following surgery, including surgery of the abdomen, the bowel dysfunction may become quite severe, lasting for more than a week and affecting more than one portion of the GI tract. This condition is often referred to as post-surgical (or post-operative) paralytic ileus and most frequently occurs after laparotomy (see Livingston, E. H. and Passaro, E. D. Jr. *Digestive Diseases and Sciences* 1990, 35, 121). Similarly, post-partum ileus is a common problem for women in the period following childbirth, and is thought to be caused by similar fluctuations in natural opioid levels as a result of birthing stress.

As used herein, the term "patient" refers to animals, including mammals, preferably humans.

As used herein, the term "side effect" refers to a consequence other than the one(s) for which an agent or measure is used, as the adverse effects produced by a drug, especially on a tissue or organ system other then the one sought to be benefited by its administration. In the case, for example, of opioids, the term "side effect" may refer to such conditions as, for example, constipation, nausea and/or vomiting.

When any variable occurs more than one time in any constituent or in any formula, its definition in each occurrence is independent of its definition at every other occurrence. Combinations of substituents and/or variables are permissible only if such combinations result in stable compounds.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical or geometric isomer, except where such stereochemistry is clearly defined.

In certain preferred embodiments, the compounds, pharmaceutical compositions and methods of the present invention may involve a opioid antagonist compound. The term "peripheral" designates that the compound acts primarily on physiological systems and components external to the central nervous system. In preferred form, the opioid antagonist compounds employed in the methods of the present invention exhibit high levels of activity with respect to peripheral tissue, such as, gastrointestinal tissue, while exhibiting reduced, and preferably substantially no, CNS activity. The phrase "substantially no CNS activity," as used herein, means that less than about 50% of the pharmacological activity of the compounds employed in the present methods is exhibited in the CNS, preferably less than about 25%, more preferably less than about 10%, even more preferably less than about 5% and most preferably 0% of the pharmacological activity of the compounds employed in the present methods is exhibited in the CNS.

Furthermore, it is preferred in certain embodiments of the invention that the opioid antagonist compound does not substantially cross the blood-brain barrier. The phrase "does not substantially cross," as used herein, means that less than about 20% by weight of the compound employed in the present methods crosses the blood-brain barrier, preferably less than about 15% by weight, more preferably less than about 10% by weight, even more preferably less than about 5% by weight and most preferably 0% by weight of the compound crosses the blood-brain barrier. Selected compounds can be evaluated for CNS penetration by determining plasma and brain levels following i.v. administration.

Accordingly, in one embodiment, the present invention provides compounds of formula I:

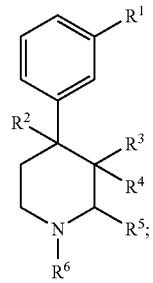

wherein:

$R^1$ is —$OR^7$, —$NR^7R^8$, —$COOR^7$, —$CONR^7R^8$, or —$CH_2OH$;

each $R^7$ is independently H, alkyl, cycloalkyl, alkylcycloalkyl, or aralkyl;

each $R^8$ is independently H, alkyl, aralkyl, or aryl;

$R^2$, $R^3$, $R^4$, and $R^5$ are selected such that:

$R^2$ and $R^5$ together form —$(CH_2)_q$—, where q is 2 to 4, $R^3$ is alkyl, and $R^4$ is H; or $R^2$ and $R^3$ together with the carbon atoms to which they are attached form a fused carbocycle, $R^4$ is alkyl, and $R^5$ is H;

$R^6$ is H or —$(CHR^9)_mW$;

each $R^9$ is independently H, alkyl, cycloalkyl, alkylcycloalkyl, aryl, aralkyl or heteroaryl;

W is H, alkyl, cycloalkyl, alkylcycloalkyl, heterocycloalkyl, alkylheterocycloalkyl, aryl, heteroaryl, —$CH_2OH$, —$CH_2OR^7$, or —$C(=O)R^{10}$;

$R^{10}$ is —$OR^7$ or —$NR^7R^{11}$;

$R^{11}$ is H, alkyl, aralkyl, aryl or —$(CHR^9)_nC(=O)R^{12}$;

$R^{12}$ is —$OR^7$ or —$NR^7R^8$;

m is an integer from 1 to 4; and n is an integer from 1 to 4;

provided that when $R^1$ is —OH, then W is heterocycloalkyl, alkylheterocycloalkyl, —$CH_2OH$, or —$C(=O)R^{10}$; and when $R^1$ is —OH and W is heterocycloalkyl or alkylheterocycloalkyl in which the heterocyclic ring moiety of the heterocycloalkyl or alkylheterocycloalkyl contains only one heteroatom, wherein the heteroatom is nitrogen, then the heterocyclic ring moiety is connected to —$(CHR^9)_m$— through a heterocyclic ring carbon atom;

or a stereoisomer, prodrug, pharmaceutically acceptable salt, hydrate, solvate, acid hydrate, N-oxide or isomorphic crystalline form thereof.

In certain preferred embodiments of compounds of formula I, $R^1$ is —$OR^7$, —$NR^7R^8$, or —$CONR^7R^8$. In certain preferred embodiments when $R^1$ is —$NR^7R^8$ or —CONR⁷R⁸, at least one of R⁷, and R⁸ is H. In certain more preferred embodiments, R⁷ is H. In other preferred embodiments, R⁸ is H or alkyl.

In certain preferred embodiments of compounds of formula I, when R¹ is —CONR⁷R⁸, at least one of R⁷ and R⁸ is H. Preferably, at least one of R⁷ and R⁸ is H and the other is H or alkyl. More preferably, each of R⁷ and R⁸ is H.

In certain preferred embodiments of compounds of formula I, when R¹ is —NR⁷R⁸, at least one of R⁷ and R⁸ is H. Preferably, at least one of R⁷ and R⁸ is H and the other is H or alkyl. More preferably, each of R⁷ and R⁸ is H.

In certain more preferred embodiments of compounds of formula I, R⁸ is methyl or ethyl.

In certain preferred embodiments of compounds of formula I, R³ is methyl.

In certain preferred embodiments of compounds of formula I, R⁴ is methyl.

In other preferred embodiments of compounds of formula I, R², R³, R⁴, and R⁵ are selected such that R² and R⁵ together form —(CH₂)$_q$—, where q is 2 to 4, R³ is alkyl, and R⁴ is H. In some preferred embodiments, R³ is methyl. More preferably, q is 3.

In other preferred embodiments of compounds of formula I, R², R³, R⁴ and R⁵ are selected such that R² and R³ together with the carbon atoms to which they are attached form a fused carbocycle, R⁴ is alkyl and R⁵ is H. In some preferred embodiments, R⁴ is methyl. More preferably, the fused carbocycle is tetrahydroindene, tetrahydronaphthalene, or tetrahydroanthracene. Even more preferably, the fused carbocycle is tetrahydronaphthalene.

In certain preferred embodiments of compounds of formula I, R⁶ is —(CHR⁹)$_m$W.

In certain more preferred embodiments of compounds of formula I,

R⁶ is:

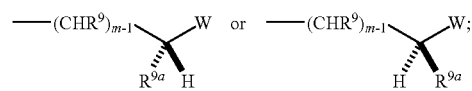

wherein R⁹ᵃ is H, alkyl, cycloalkyl, alkylcycloalkyl, aryl, aralkyl or heteroaryl. More preferably, R⁹ᵃ is aralkyl. Even more preferably, R⁹ᵃ is benzyl. In certain even more preferred embodiments of compounds of formula I, R⁶ is:

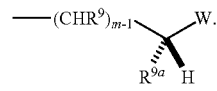

In other even more preferred embodiments of compounds of formula I, R⁶ is:

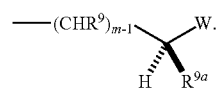

In certain preferred embodiments of compounds of formula I, each R⁹ is independently H or aralkyl. More preferably, R⁹ is aralkyl. Even more preferably, R⁹ is benzyl.

In some preferred embodiments of compounds of formula I, W is aryl, —CH₂OH, or —C(=O)R¹⁰.

In still other preferred embodiments of compounds of formula I, R¹⁰ is —OH or —NR⁷R¹¹. More preferably, when R¹⁰ is —NR⁷R¹¹, R⁷ is H.

In yet other preferred embodiments of compounds of formula I, R¹¹ is —(CHR⁹)$_n$C(=O)R¹². More preferably, when R¹¹ is —(CHR⁹)$_n$C(=O)R¹², R¹² is —OH or —NR⁷R⁸.

In still other preferred embodiments of compounds of formula I, m is the integer 1 or 2.

In still other preferred embodiments of compounds of formula I, n is the integer 1 or 2. More preferably, n is 1.

In other preferred embodiments, the compounds of formula I have the formula II:

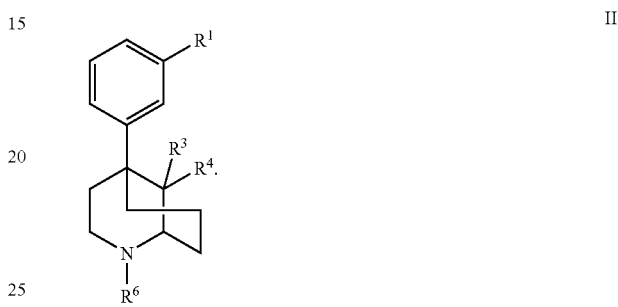

In other preferred embodiments, the compounds of formula I have the formula IIIa or IIIb:

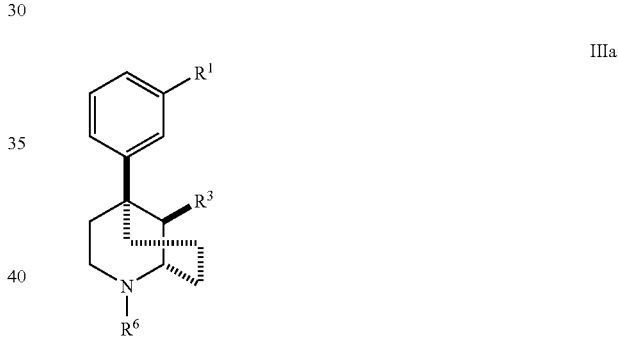

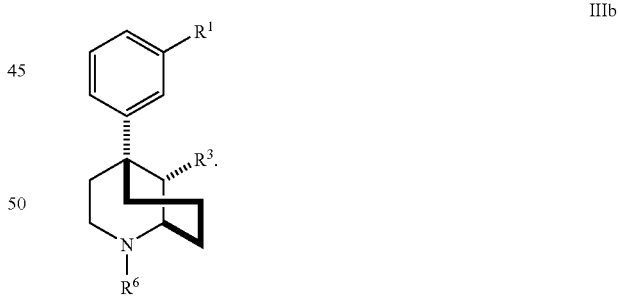

More preferably, the compounds of formula I are of formula IIIa. More preferably still, when compounds of formula I are of formula IIIa, R¹ is —OR⁷, —NR⁷R⁸, or —CONR⁷R⁸. Still more preferably, when compounds are of formula IIIa and R¹ is —OR⁷, —NR⁷R⁸, or —CONR⁷R⁸, then R⁶ is

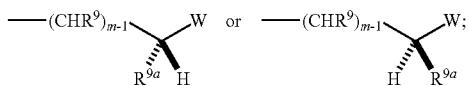

and $R^{9a}$ is H, alkyl, cycloalkyl, alkylcycloalkyl, aryl, aralkyl or heteroaryl. Yet more preferably, when compounds of formula I are of formula IIIa, $R^1$ is —$OR^7$, —$NR^7R^8$ or —$CONR^7R^8$;
$R^6$ is:

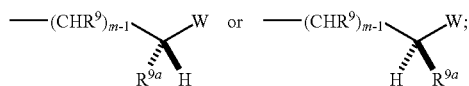

and

W is aryl, —$CH_2OH$, or —$C(=O)R^{10}$.

In certain preferred embodiments, $R^2$ and $R^3$ together with the carbon atoms to which they are attached form a fused carbocycle. Preferably, tetrahydroindene, tetrahydronaphthalene, or tetrahydroanthracene, and more preferably, tetrahydronaphthalene.

In yet other preferred embodiments, the compounds of formula I have the formula IV:

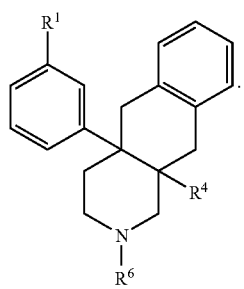

IV

In yet other preferred embodiments, the compounds of formula I have the formula Va or Vb:

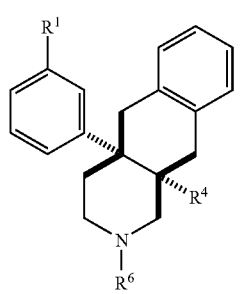

Va

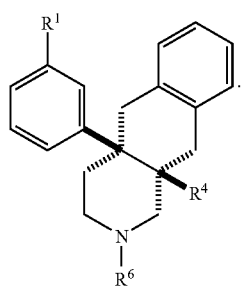

Vb

In another preferred embodiment of compounds of formula IIIa,
$R^6$ is —$(CHR^9)_mW$;
W is —$C(=O)R^{10}$;
$R^{10}$ is —$OR^7$;
$R^1$ is —$NR^7R^8$;
$R^7$, $R^8$ and $R^9$ are each H;
$R^3$ is methyl,
$R^{9a}$ is benzyl; and
m is 2.

In another preferred embodiment of compounds of formula IIIa,
$R^6$ is —$(CHR^9)_mW$;
W is phenyl;
$R^1$ is —$C(=O)NR^7R^8$;
$R^3$ is methyl;
$R^7$, $R^8$, $R^9$ and $R^{9a}$ are each H; and
m is 2.

In another preferred embodiment of compounds of formula IIIa,
$R^6$ is:

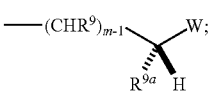

W is —$CH_2OH$;
$R^1$ is —$NR^7R^8$;
$R^3$ is methyl;
$R^7$ and $R^9$ are each H;
$R^8$ is —$CH_2CH_3$;
$R^{9a}$ is benzyl; and
m is 2.

In another preferred embodiment of compounds of formula IIIa,
$R^6$ is:

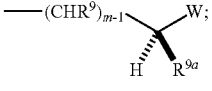

W is —$CH_2OH$;
$R^1$ is —$NR^7R^8$;
$R^3$ is methyl;
$R^7$ and $R^9$ are each H;
$R^8$ is —$CH_2CH_3$;
$R^{9a}$ is benzyl; and
m is 2

In another preferred embodiment of compounds of formula IIIa,
$R^6$ is:

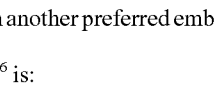

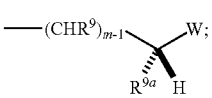

$R^1$ is —$OR^7$;
W is —$C(=O)R^{10}$;
$R^{10}$ is —$OR^7$;
$R^3$ is methyl;

each $R^7$ and $R^9$ is H;
$R^{9a}$ is benzyl; and
m is 2.

In another preferred embodiment of compounds of formula IIIa,
$R^6$ is:

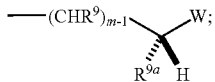

$R^1$ and $R^{12}$ are each —$OR^7$;
W is —C(=O)$R^{10}$;
$R^{10}$ is —$NR^7R^{11}$;
$R^3$ is methyl;
each $R^7$ and each $R^9$ is H;
$R^{9a}$ is benzyl;
$R^{11}$ is —(CH$R^9$)$_n$C(=O)$R^{12}$;
m is 2; and
n is 1.

In another preferred embodiment of compounds of formula Va or Vb, $R^6$ is:

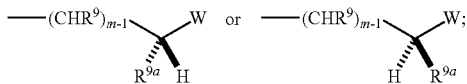

$R^{9a}$ is H, alkyl, cycloalkyl, alkylcycloalkyl, aryl, aralkyl or heteroaryl.

More preferably the compound has the formula Vb,
$R^6$ is:

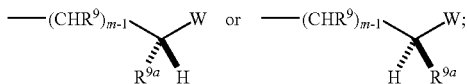

and
$R^{9a}$ is H, alkyl, cycloalkyl, alkylcycloalkyl, aryl, aralkyl or heteroaryl;
$R^1$ is C(=O)$NR^7R^8$;
$R^4$ is methyl;
$R^7$, $R^8$, $R^9$, and $R^{9a}$ are each H;
W is phenyl; and
m is 2.

In another preferred embodiment of compounds of formula Va,
$R^6$ is:

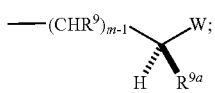

$R^1$ and $R^{10}$ are each —$OR^7$;
$R^4$ is methyl;
$R^7$ and $R^9$ are each H;
$R^{9a}$ is benzyl;
W is —C(=O)$R^{10}$; and
m is 2.

In another preferred embodiment of compounds of formula Va,
$R^6$ is:

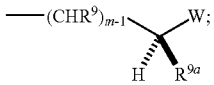

$R^1$ and $R^{12}$ are each —$OR^7$;
$R^4$ is methyl;
$R^7$ and $R^9$ are each H;
$R^{9a}$ is benzyl;
W is —C(=O)$R^{10}$;
$R^{10}$ is —$NR^7R^{11}$;
$R^{11}$ is —(CH$R^9$)$_n$C(=O)$R^{12}$;
n is 1; and
m is 2.

In certain preferred embodiments of compounds of formula I, the compound is:
2-benzyl-3-[5-(3-hydroxy-phenyl)-9-methyl-2-aza-bicyclo[3.3.1]non-2-yl]-propionic acid;
{2-benzyl-3-[5-(3-hydroxy-phenyl)-9-methyl-2-aza-bicyclo[3.3.1]non-2-yl]-propionylamino}acetic acid;
2-benzyl-3-[5-(3-ethylamino-phenyl)-9-methyl-2-aza-bicyclo[3.3.1]non-2-yl]-propan-1-ol;
2-benzyl-3-[5-(3-ethylamino-phenyl)-9-methyl-2-aza-bicyclo[3.3.1]non-2-yl]-propan-1-ol;
3-[5-(3-amino-phenyl)-9-methyl-2-aza-bicyclo[3.3.1]non-2-yl]-2-benzyl-propionic acid;
3-[9-methyl-2-phenylethyl-2-aza-bicyclo[3.3.1]non-5-yl]-benzamide;
2-benzyl-3-[4a-(3-hydroxy-phenyl)-10a-methyl-3,4,4a,5,10,10a-hexahydro-1H-benzo[g]isoquinolin-2-yl]-propionic acid;
{2-benzyl-3-[4a-(3-hydroxy-phenyl)-10a-methyl-3,4,4a,5,10,10a-hexahydro-1H-benzo[g]isoquinolin-2-yl]-propionylamino}-acetic acid; or
3-(10a-methyl-2-phenethyl-1,3,4,5,10,10a-hexahydro-2H-benzo[g]isoquinolin-4a-yl)-benzamide;
or stereoisomers thereof.

In certain preferred embodiments of compounds of formula I, the compound is
2(S)-benzyl-3-[5-(3-hydroxy-phenyl)-9-methyl-2-aza-bicyclo[3.3.1]non-2-yl]-propionic acid;
{2(S)-benzyl-3-[5-(3-hydroxy-phenyl)-9-methyl-2-aza-bicyclo[3.3.1]non-2-yl]-propionylamino}acetic acid;
2(S)-benzyl-3-[5-(3-ethylamino-phenyl)-9-methyl-2-aza-bicyclo[3.3.1]non-2-yl]-propan-1-ol; or
2(R)-benzyl-3-[5-(3-ethylamino-phenyl)-9-methyl-2-aza-bicyclo[3.3.1]non-2-yl]-propan-1-ol;
or partial stereoisomers thereof.

In yet other embodiments, the invention is directed to methods for binding opioid receptors in a patient in need thereof, comprising the step of:
administering to the patient a composition comprising an effective amount of a compound of formula I. In some preferred embodiments, the opioid receptors are μ, κ, or δ. In certain more preferred embodiments wherein μ opioid receptors are bound, the receptors are located in the central nervous system; in other embodiments the receptors are located peripherally to the central nervous system. In certain other more preferred embodiments wherein κ opioid receptors are bound, the receptors are located in the central nervous system; in other embodiments the receptors are located peripherally to the central nervous system. In still other more preferred embodiments wherein δ opioid receptors are bound, the receptors are located in the central nervous system; in other embodiments the receptors are located peripherally to the central nervous system. In still other preferred embodiments of methods that bind opioid receptors in a patient in need thereof, the binding antagonizes the activity of the opioid receptors. In some preferred embodiments of methods that bind opioid receptors in a patient in need thereof, the compound administered exhibits activity toward the opioid receptors. In some more preferred embodiments, the compound administered does not substantially cross the blood-brain barrier.

In certain embodiments of methods that bind opioid receptors in a patient in need thereof, comprising the step of:

administering to the patient a composition comprising an effective amount of a compound of formula I, the patient is in need of prevention or treatment of a condition or disease caused by an opioid. The opioid may be endogenous or exogenous. In certain preferred embodiments, the composition further comprises an effective amount of at least one opioid.

In other embodiments, the invention is directed to methods of preventing or treating gastrointestinal dysfunction, comprising the step of:

administering to a patient in need thereof, a composition comprising an effective amount of a compound of formula I.

In yet other embodiments, the invention is directed to methods of preventing or treating ileus, comprising the step of:

administering to a patient in need thereof, a composition comprising an effective amount of a compound of formula I. Preferably, the ileus is post-operative ileus.

In yet other embodiments, the invention is directed to methods of preventing or treating obesity, comprising the step of:

administering to a patient in need thereof, a composition comprising an effective amount of a compound of formula I.

In other embodiments, the invention is directed to methods of preventing or treating a side effect associated with an opioid, comprising the step of:

administering to a patient in need thereof, a composition comprising an effective amount of a compound of formula I.

In certain preferred embodiments, the side effect is selected from the group consisting of constipation, nausea, vomiting, and combinations thereof. In other preferred embodiments, the administering step occurs before, during or after a step of administering at least one opioid. Even more preferred, the opioid that is administered is alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol or mixtures thereof In yet other embodiments, the invention is directed to methods of preventing or treating pain, comprising the step of:

administering to a patient in need thereof, a composition, comprising:

an effective amount of an opioid; and an effective amount of a compound of formula I.

In certain more preferred embodiments, the opioid is alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol or mixtures thereof.

The compounds employed in the methods of the present invention may exist in prodrug form. As used herein, "prodrug" is intended to include any covalently bonded carriers which release the active parent drug, for example, as according to formula I or other formulas or compounds employed in the methods of the present invention in vivo when such prodrug is administered to a mammalian subject. Since prodrugs are known to enhance numerous desirable qualities of pharmaceuticals (e.g., solubility, bioavailability, manufacturing, etc.) the compounds employed in the present methods may, if desired, be delivered in prodrug form. Thus, the present invention contemplates methods of delivering prodrugs. Prodrugs of the compounds employed in the present invention, for example formula I, may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

The compounds employed in the methods of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As discussed in detail above, compounds employed in the present methods may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present may contain protecting groups during the course of synthesis. Protecting groups are known per se as chemical functional groups that can be selectively appended to and removed from functionalities, such as hydroxyl groups and carboxy groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl group. Other preferred protecting groups that may be employed in accordance with the present invention may be described in Greene, T. W. and Wuts, P. G. M., *Protective Groups in Organic Synthesis* 3d. Ed., Wiley & Sons, 1991.

While not intending to be bound by any theory or theories of operation, it is contemplated that opioid side effects, such as constipation, vomiting and nausea, may result from undesirable interaction of the opioid with peripheral opioid receptors, such as peripheral μ receptors. Administration of the compounds of formula I according to one aspect of the present invention may block interaction of the opioid compounds with the peripheral receptors, thereby preventing and/or inhibiting the side effects, while preferably not interfering with the therapeutic effect of the opioid in the CNS.

When any variable occurs more than one time in any constituent or in any formula, its definition in each occurrence is independent of its definition at every other occurrence. Combinations of substituents and/or variables are permissible only if such combinations result in stable compounds.

In accordance with certain embodiments of the present invention, there are provided methods that comprise administering to a patient, inter alia, an opioid compound. A wide variety of opioids is available that may be suitable for use in the present methods and compositions. Generally speaking, it is only necessary that the opioid provide the desired effect (for example, pain alleviation), and be capable of being incorporated into the present combination products and methods (discussed in detail below). In preferred embodiments, the present methods and compositions may involve an opioid that is selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil and/or tramadol. More preferably, the opioid is selected from morphine, codeine, oxycodone, hydrocodone, dihydrocodeine, propoxyphene, fentanyl, tramadol, and mixtures thereof.

The opioid component of the present compositions may further include one or more other active ingredients that may be conventionally employed in analgesic and/or cough-cold-antitussive combination products. Such conventional ingredients include, for example, aspirin, acetaminophen, phenylpropanolamine, phenylephrine, chlorpheniramine, caffeine, and/or guaifenesin. Typical or conventional ingredients that may be included in the opioid component are described, for example, in the *Physicians' Desk Reference,* 1999, the disclosure of which is hereby incorporated herein by reference, in its entirety.

In addition, the opioid component may further include one or more compounds that may be designed to enhance the analgesic potency of the opioid and/or to reduce analgesic tolerance development. Such compounds include, for example, dextromethorphan or other NMDA antagonists (Mao, M. J., et al., *Pain,* 1996, 67, 361), L-364,718 and other CCK antagonists (Dourish, C. T., et al., *Eur. J. Pharmacol.,* 1988, 147, 469), NOS inhibitors (Bhargava, H. N., et al., *Neuropeptides,* 1996, 30, 219), PKC inhibitors (Bilsky, E. J., et al., *J. Pharmacol. Exp. Ther.,* 1996, 277, 484), and dynorphin antagonists or antisera (Nichols, M. L., et al., *Pain,* 1997, 69, 317). The disclosures of each of the foregoing documents are hereby incorporated herein by reference, in their entireties.

Other opioids, optional conventional opioid components, and optional compounds for enhancing the analgesic potency of the opioid and/or for reducing analgesic tolerance development, that may be employed in the methods and compositions of the present invention, in addition to those exemplified above, would be readily apparent to one of ordinary skill in the art, once armed with the teachings of the present disclosure.

Another embodiment of the invention provides a pharmaceutical composition comprising a pharmaceutically acceptable carrier and an effective amount of a compound of formula I.

Although the compounds of the present invention may be administered as the pure chemicals, it is preferable to present the active ingredient as a pharmaceutical composition. The invention thus further provides a pharmaceutical composition comprising one or more of the compounds of formula I, together with one or more pharmaceutically acceptable carriers therefore and, optionally, other therapeutic and/or prophylactic ingredients. The carrier(s) must be acceptable in the sense of being compatible with the other ingredients of the composition and not deleterious to the recipient thereof.

The compounds of the invention may be administered in an effective amount by any of the conventional techniques well-established in the medical field. The compounds employed in the methods of the present invention including, for example, opioid and the compounds of formula I, may be administered by any means that results in the contact of the active agents with the agents' site or site(s) of action in the body of a patient. The compounds may be administered by any conventional means available for use in conjunction with pharmaceuticals, either as individual therapeutic agents or in a combination of therapeutic agents. For example, they may be administered as the sole active agents in a pharmaceutical composition, or they can be used in combination with other therapeutically active ingredients.

The compounds are preferably combined with a pharmaceutical carrier selected on the basis of the chosen route of administration and standard pharmaceutical practice as described, for example, in *Remington's Pharmaceutical Sciences* (Mack Pub. Co., Easton, Pa., 1980), the disclosures of which are hereby incorporated herein by reference, in their entirety.

Compounds of the present invention can be administered to a mammalian host in a variety of forms adapted to the chosen route of administration, e.g., orally or parenterally. Parenteral administration in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. The amount of active compound(s) in such therapeutically useful compositions is preferably such that a suitable dosage will be obtained. Preferred compositions or preparations according to the present invention may be prepared so that an oral dosage unit form contains from about 0.1 to about 1000 mg of active compound.

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The active compound may also be administered parenterally or intraperitoneally. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compounds in the required amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and the freeze drying technique that yields a powder of the active ingredient, plus any additional desired ingredient from the previously sterile-filtered solution thereof.

The therapeutic compounds of this invention may be administered to a patient alone or in combination with a pharmaceutically acceptable carrier. As noted above, the relative proportions of active ingredient and carrier may be determined, for example, by the solubility and chemical nature of the compounds, chosen route of administration and standard pharmaceutical practice.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. Generally speaking, oral administration may require higher dosages.

The combination products of this invention, such as pharmaceutical compositions comprising opioids in combination with the compounds of formula I, may be in any dosage form, such as those described herein, and can also be administered in various ways, as described herein. In a preferred embodiment, the combination products of the invention are formulated together, in a single dosage form (that is, combined together in one capsule, tablet, powder, or liquid, etc.). When the combination products are not formulated together in a single dosage form, the opioid compounds and the compounds of formula I may be administered at the same time (that is, together), or in any order. When not administered at the same time, preferably the administration of an opioid and the compounds of formula I occurs less than about one hour apart, more preferably less than about 30 minutes apart, even more preferably less than about 15 minutes apart, and still more preferably less than about 5 minutes apart. Preferably, administration of the combination products of the invention is oral, although other routes of administration, as described above, are contemplated to be within the scope of the present invention. Although it is preferable that the opioids and the compounds of formula I are both administered in the same fashion (that is, for example, both orally), if desired, they may each be administered in different fashions (that is, for example, one component of the combination product may be administered orally, and another component may be administered intravenously). The dosage of the combination products of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired.

Although the proper dosage of the combination products of this invention will be readily ascertainable by one skilled in the art, once armed with the present disclosure, by way of general guidance, where an opioid compounds is combined with the compounds of formula I, for example, typically a daily dosage may range from about 0.01 to about 100 milligrams of the opioid (and all combinations and subcombinations of ranges therein) and about 0.001 to about 100 milligrams of the compounds of formula I (and all combinations and subcombinations of ranges therein), per kilogram of patient body weight. Preferably, the a daily dosage may be about 0.1 to about 10 milligrams of the opioid and about 0.01 to about 10 milligrams of the compounds of formula I per kilogram of patient body weight. Even more preferably, the daily dosage may be about 1.0 milligrams of the opioid and about 0.1 milligrams of the compounds of formula I per kilogram of patient body weight. With regard to a typical dosage form of this type of combination product, such as a tablet, the opioid compounds (e.g., morphine) generally may be present in an amount of about 15 to about 200 milligrams, and the compounds of formula I in an amount of about 0.1 to about 4 milligrams.

Particularly when provided as a single dosage form, the potential exists for a chemical interaction between the combined active ingredients (for example, an opioid and the compounds of formula I). For this reason, the preferred dosage forms of the combination products of this invention are formulated such that although the active ingredients are combined in a single dosage form, the physical contact between the active ingredients is minimized (that is, reduced).

In order to minimize contact, one embodiment of this invention where the product is orally administered provides for a combination product wherein one active ingredient is enteric coated. By enteric coating one or more of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material that effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time by the same manner, will be readily apparent to those skilled in the art, once armed with the present disclosure.

Pharmaceutical kits useful in, for example, the treatment of pain, which comprise a therapeutically effective amount of an opioid along with a therapeutically effective amount of the 3,4-disubstituted-4-aryl-piperidine compound of the invention, in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL™ two-part container (available from Abbott Labs, Chicago, Ill.), as desired. The opioid compound and the compounds of formula I may be separate, or combined into a single dosage form as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The dose may also be provided by controlled release of the compound, by techniques well known to those in the art.

The compounds of the present invention may be used in methods to bind opioid receptors, including μ, κ and δ opioid receptors. Such binding may be accomplished by contacting the receptor with an effective amount of the compound of the invention. Preferably, the contacting step conducted in an aqueous medium, preferably at physiologically relevant ionic strength, pH, and the like.

In certain preferred embodiments, the compounds of the present invention bind μ and κ opioid receptors or combinations thereof. The opioid receptors may be located in the central nervous system or located peripherally to the central nervous system or in both locations.

In certain other preferred embodiments, the compounds of the present invention bind κ opioid receptors.

In preferred embodiments of the methods of the invention, the compounds antagonize the activity of the opioid receptors. In other preferred embodiments, the compounds prevent or treat a condition or disease caused by an opioid (either endogenous or exogenous). In certain embodiments of the method, particularly where the opioid are exogenous, the compounds of the invention preferably do not substantially cross the blood-brain barrier.

The compounds of the present invention may be used in methods to antagonize μ, κ, or δ or any combinations or subcombinations of those opioid receptors, particularly where undesirable symptoms or conditions are side effects of administering exogenous opioids. Furthermore, the compounds of the invention may be used as to treat patients having disease states that are ameliorated by binding opioid receptors or in any treatment wherein temporary suppression of the μ, κ or both types of opioid receptor system is desired.

Such symptoms, conditions or diseases include the complete or partial antagonism of opioid-induced sedation, confusion, respiratory depression, euphoria, dysphoria, hallucinations, pruritus (itching), increased biliary tone, increased biliary colic, and urinary retention, ileus, emesis, and addiction liability; prevention or treatment of opioid and cocaine dependence; rapid opioid detoxification; treatment of alcoholism; treatment of alcoholic coma; detection of opioid use or abuse (pupil test); treatment of eating disorders; treatment of obesity; treatment of post-concussional syndrome; adjunctive therapy in septic, hypovolemic or endotoxin-induced shock; potentiation of opioid analgesia (especially at ultra-low doses); reversal or prevention of opioid tolerance and physical dependence (especially at ultra-low doses); prevention of sudden infant death syndrome; treatment of psychosis (especially wherein the symptoms are associated with schizophrenia, schizophreniform disorder, schizoaffective disorder, unipolar disorder, bipolar disorder, psychotic depression, Alzheimer's disease, Parkinson's disease, compulsive disorders, and other psychiatric or neurologic disorders with psychosis as symptoms); treatment of dyskinesia, treatment of autism; treatment of the endocrine system (including increased release of leutinizing hormone, treatment of infertility, increasing number of multiple births in animal husbandry, and male and female sexual behavior); treatment of the immune system and cancers associated with binding of the opioid receptors; treatment of anxiolysis; treatment of diuresis; treatment and regulation of blood pressure; treatment of tinnitus or impaired hearing; treatment of epilepsy; treatment of cachexia; treatment of general cognitive dysfunctions; and treatment of kleptomania.

The compounds of the invention present invention may also be used as cytostatic agents, as antimigraine agents, as immunomodulators, as immunosuppressives, as antiarthritic agents, as antiallergic agents, as virucides, to treat diarrhea, antipsychotics, as antischizophrenics, as antidepressants, as uropathic agents, as antitussives, as antiaddictive agents, as anti-smoking agents, to treat alcoholism, as hypotensive agents, to treat and/or prevent paralysis resulting from traumatic ischemia, general neuroprotection against ischemic trauma, as adjuncts to nerve growth factor treatment of hyperalgesia and nerve grafts, as anti-diuretics, as stimulants, as anti-convulsants, or to treat obesity. Additionally, the present compounds may be used in the treatment of Parkinson's disease as an adjunct to L-dopa for treatment dyskinesia associated with the L-dopa treatment.

In certain preferred embodiments, the compounds of the invention may be used in methods for preventing or treating gastrointestinal dysfunction, including, but not limited to, irritable bowel syndrome, opioid-bowel dysfunction, colitis, post-operative and opioid-induced emesis (nausea and vomiting), decreased gastric motility and emptying, inhibition of small and/or large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, abdominal or epigastric pain and discomfort, constipation, and delayed absorption of orally administered medications or nutritive substances.

In certain preferred embodiments, the compounds of the invention may be used in methods for preventing or treating post-operative or opioid-induced ileus.

In other preferred embodiments, the compounds of the invention may be used in an effective amount in a method in combination with an effective amount of an opioid to treat pain.

The compounds of the invention may be administered before, during or after administering at least one opioid. The methods of the invention are particularly effective for opioids, including alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol and mixtures thereof.

Methods of Preparation

The racemic amine (+/−)2 may be prepared according to a procedure described previously [Thomas, et al., *J. Med. Chem.* 1998, 41, 4143-4149; WO 99/45925]. The two enantiomers (+)2a and (−)2b separated by chiral column may be used for the preparation of each antipode of target compound 8 (Example 2), constrained analog of Alvimopan [Note: the absolute stereochemistry for (+)2a and (−)2b has not been determined]. The synthesis of 8 from (+)2a is outlined in Scheme 1. A key step of the sequence is the 1,4-addition of (+)2a to the chiral Baylis-Hillman ester 1a [Werner, et al., *J. Org. Chem.*, 1996, 61, 587-597. Perlmutter, et al., *J. Org. Chem.*, 1995, 60, 6515-22; Perlmutter, et al., *Tetrahedron Lett.*, 1988, 29, 949-952; Drewes, et al. *Tetrahedron: Asymmetry*, 1992, 3, 255-260]. The racemic Baylis-Hillman 1 may be obtained by condensation of benzaldehyde with methyl acrylate in the presence of 1,4-diazabicyclo[2.2.2]octane (DABCO).

In the examples, the enantiomers 1a and 1b were separated on chiral column. The absolute configuration of 1a was established based on literature data [Drewes, et al., *Tetrahedron: Asymmetry*, 1992, 3, 255-260]. The conjugate addition of (+)2a to 1a in methanol at room temperature proceeded with high diastereoselectivity in favor to the anti addition product 3a(3a/3b=4.4:1, ratio determined by HPLC). Condensation of 3a with acetic anhydride in the presence of triethylamine provided the diacetate intermediate 4, which was converted to 5 by hydrogenation conducted in the presence of palladium hydroxide (Pearlman's catalyst). Hydrolysis of 5 under basic conditions provides the acid 6 (Example 1). Conversion of the acid 6 to the target compound 8 (Example 2) was completed using a O-(7-azabenzotriazol-1-yl)-N,N,N',N'-tetramethyluronium hexafluorophosphate (HATU)-mediated coupling of glycine t-butyl ester, followed by hydrolysis of the t-butyl ester intermediate 7 with concentrated hydrochloric acid in dioxane.

The preparation of Examples 3-5 (17-19) is outlined in Scheme 2. Condensation of paraformaldehyde with benzyl malonic acid 9 in the presence of diethylamine provided in high yield the acrylic acid derivative 10, which was converted to the corresponding methyl ester 11 by treatment in methanol in the presence of thionyl chloride. The conjugate addition of the racemic amine (+/−) 2 to the methyl acrylate derivative 11 afforded the desired 1,4-addition product 12 present as mixture of diastereoisomers. The triflate 13 was obtained by condensation of 12 with N-phenyltrifluoromethanesulfonimide in dichloromethane in the presence of triethylamine. The aniline derivative 15 was obtained in 2 steps from the triflate 13. Palladium catalyzed condensation of benzophenone imine with the triflate 13 afforded the imine 14, which was converted to the aniline derivative 15 by treatment with hydroxylamine hydrochloride. Condensation of the aniline derivative 15 with acetyl chloride in the presence of triethylamine afforded the acetamide 16, which was reduced to the pair of amino alcohols 17 (Example 3) and 18 (Example 4) in the presence of borane. The diastereoisomers 17 (Example 3) and 18 (Example 4) were separated by flash column chromatography. Acidic hydrolysis of the ester 15 afforded the desired carboxylic acid 19 (Example 5).

The preparation of carboxamide derivatives, such as example 6, is shown in Scheme 3. Condensation of (+/−) 2 with phenylacetic acid in the presence of BOP provided the amide 20, which was reduced to the amine 21 using borane. The intermediate 21 was then converted to the triflate 22 using N-phenyltrifluoromethanesulfonimide as triflic agent. Palladium catalyzed carbonylation of 22 provided the methyl ester 23, which was hydrolyzed under basic conditions to give the carboxylic acid 24. Coupling of 24 with ammonium chloride in the presence of triethylamine, EDCI and HOBt afforded the carboxamide 25 (Example 6).

The preparation of the fused benzocycle derivatives, e.g., Examples 7 and 8 is shown in Scheme 4. The synthesis of the amine (+/−)26 (racemic) has been described previously WO 99/45925. The two enantiomers (+)26a and (−)26b separated on chiral column can be used for the preparation of each enantiomer of target compound 32 (Example 8). Conjugate addition of (−)26b to 1a in methanol at room temperature proceeds with high diastereoselectivity in favor to the anti addition product 27a. The absolute stereochemistry of 27a as indicated in Scheme 4 was established using X-ray crystallography. The absolute stereochemistry of (+)26a and (−)26b was determined by inference to 27a. Condensation of 27a with acetic anhydride in the presence of triethylamine provided the diacetate intermediate 28, which was converted to 29 by hydrogenation. Hydrolysis of 29 in basic conditions provided the acid 30 (Example 7). Conversion of the acid 30 to the target compound 32 (Example 8) was completed using a HATU-mediated coupling of glycine t-butyl ester, followed by hydrolysis of the t-butyl ester intermediate 31 with concentrated HCl in dioxane.

The preparation of the fused benzocycle carboxamide derivatives, e.g., Example 9 is shown in Scheme 5. Condensation of (+) 26a with phenylacetic acid in the presence of BOP provided the amide 33, which was reduced to the amine 34 using borane. The intermediate 34 was then converted to the triflate 35 using N-phenyltrifluoromethanesulfonimide as triflic agent. Palladium catalyzed carbonylation of 35 provided the methyl ester 36, which was hydrolyzed under basic conditions to give the carboxylic acid 37. Coupling of 37 with ammonium chloride in the presence of triethylamine, EDCI and HOBt afforded the carboxamide 38 (Example 9).

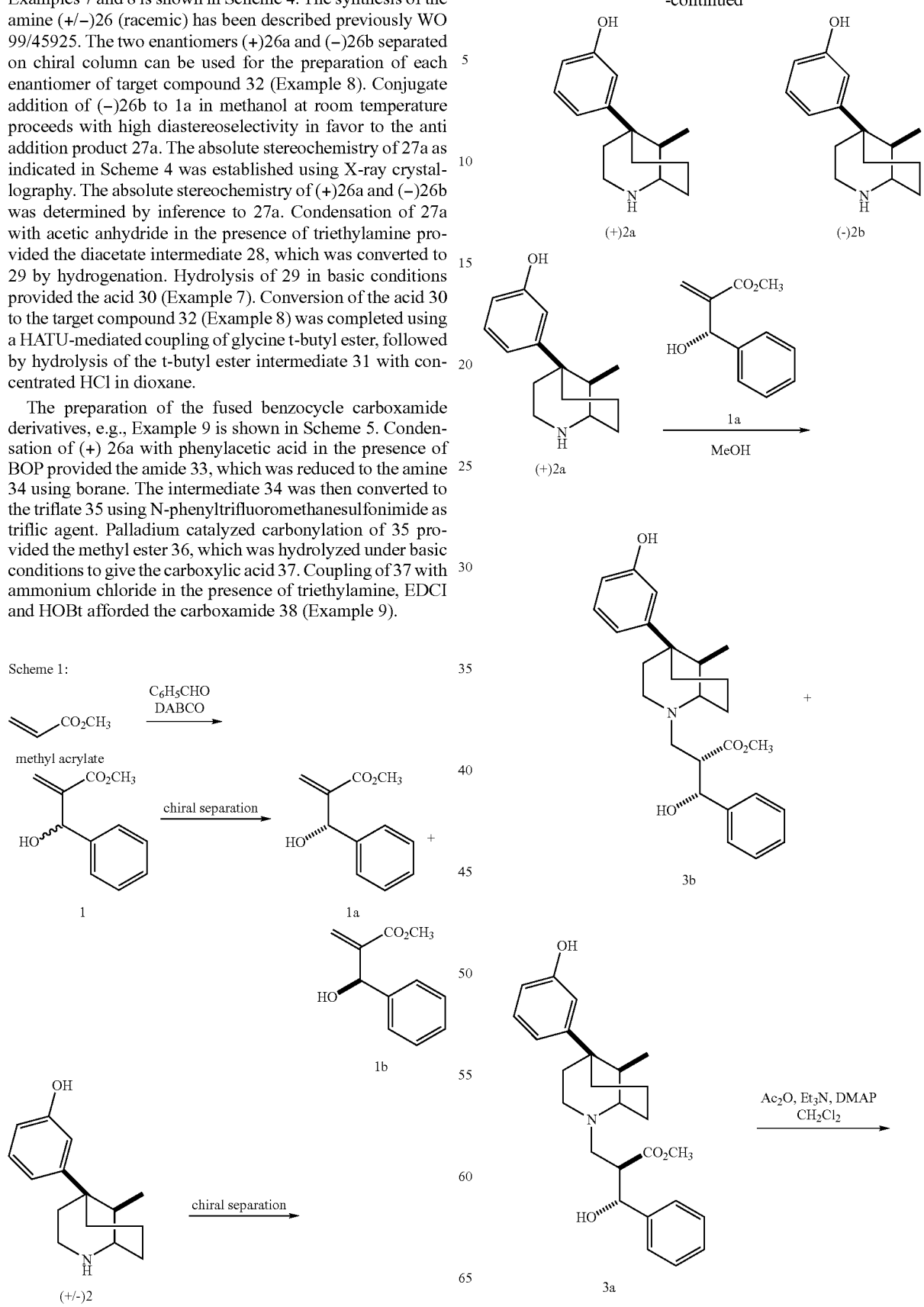

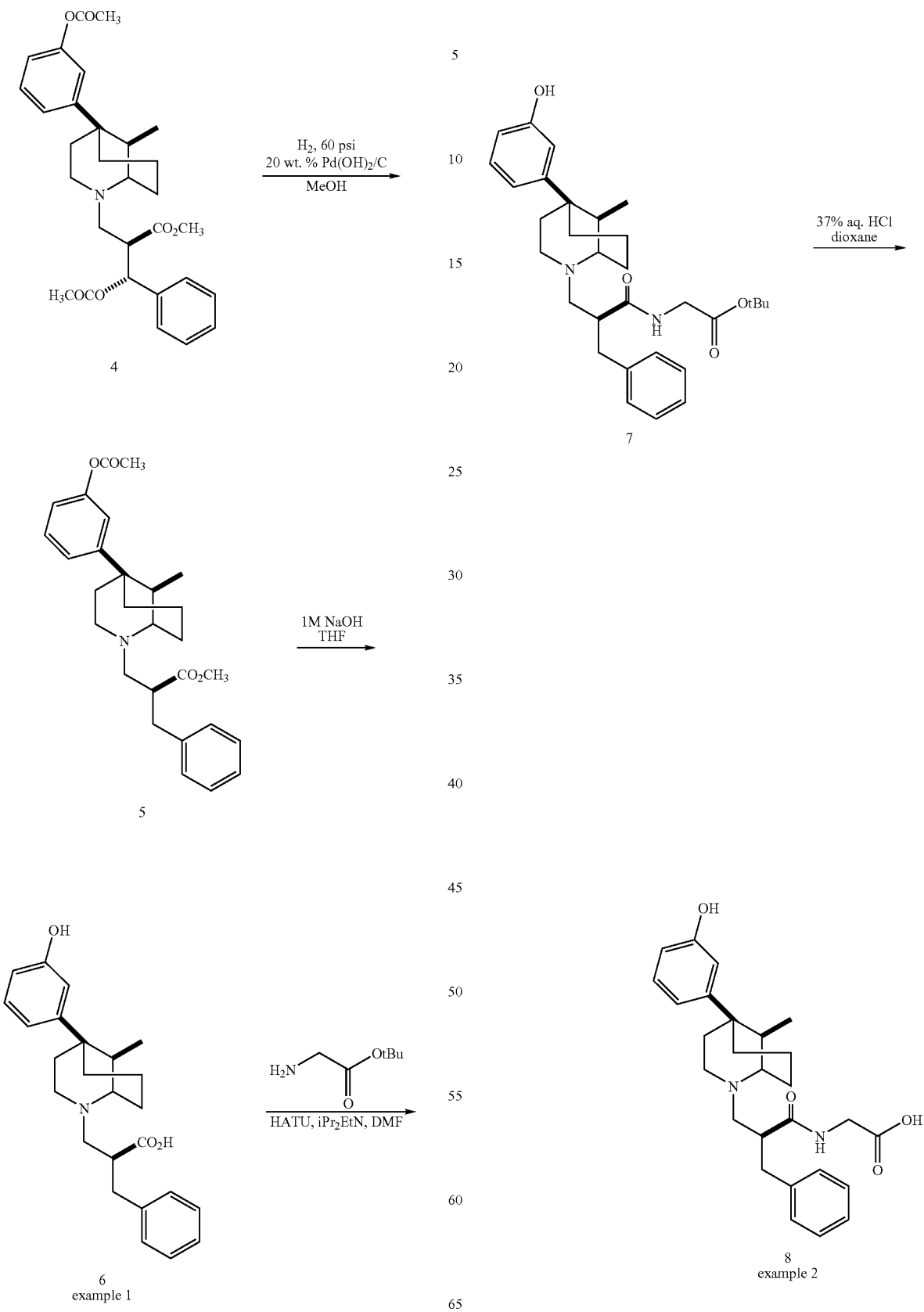

Scheme 2:
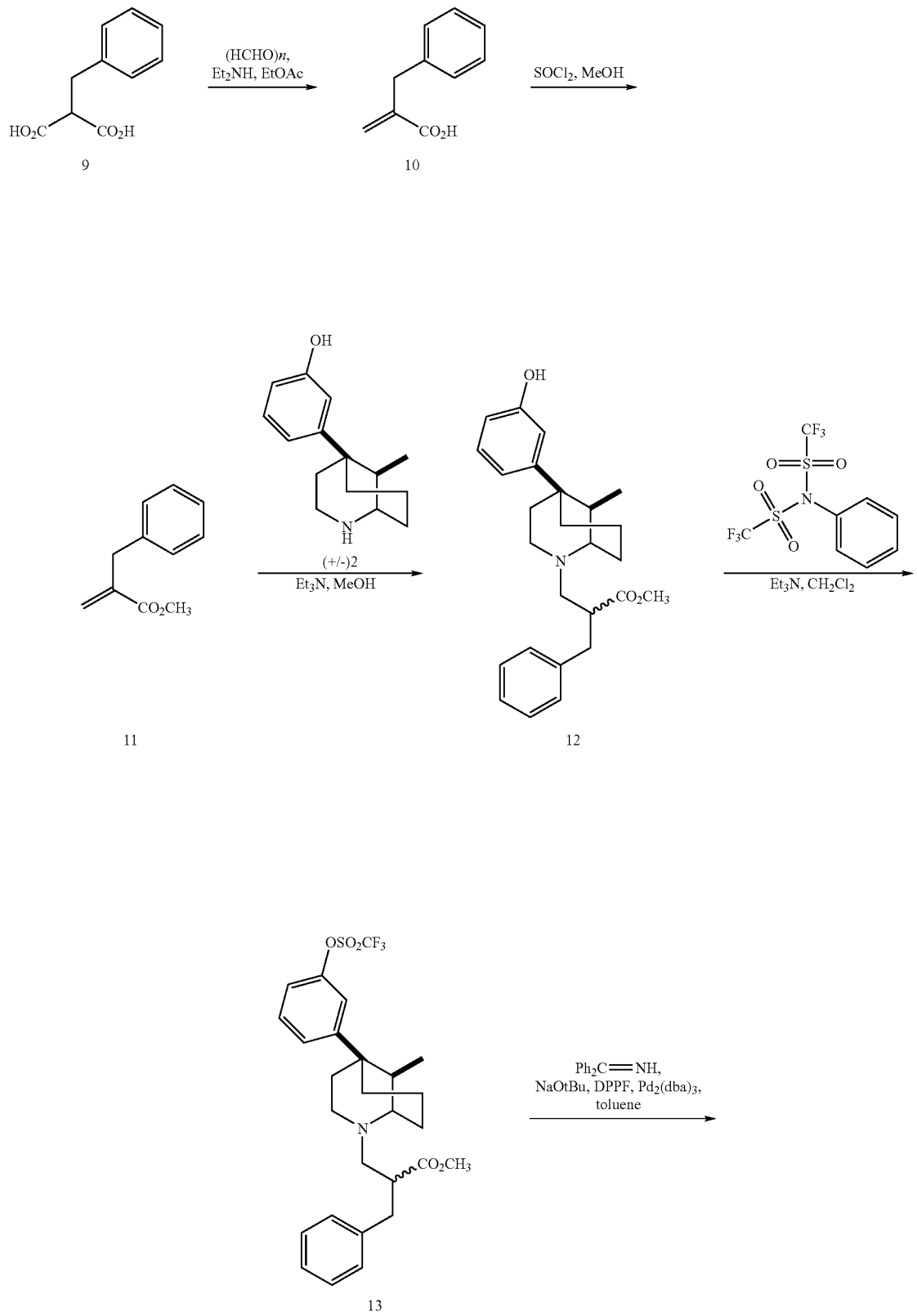

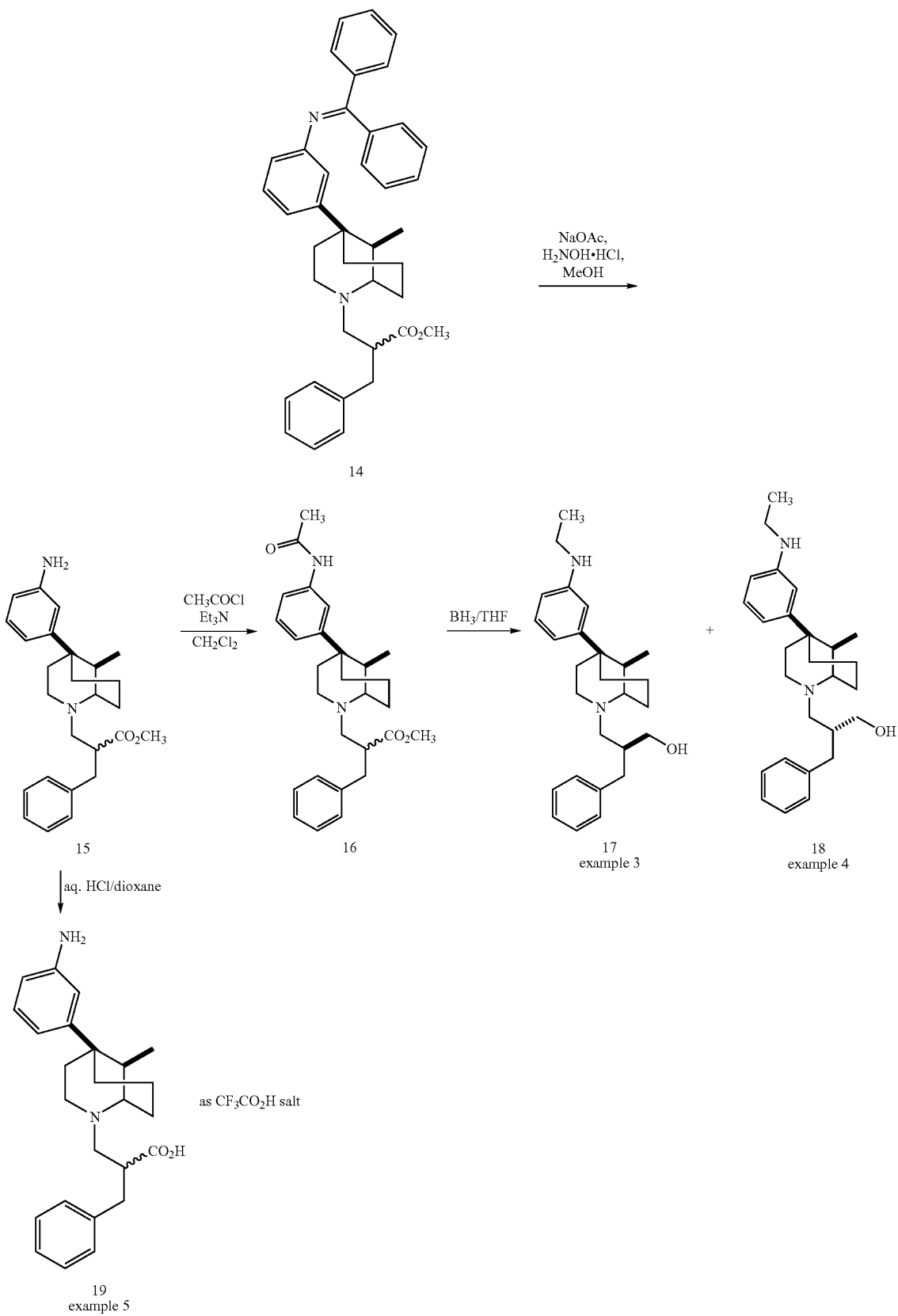

Scheme 3:
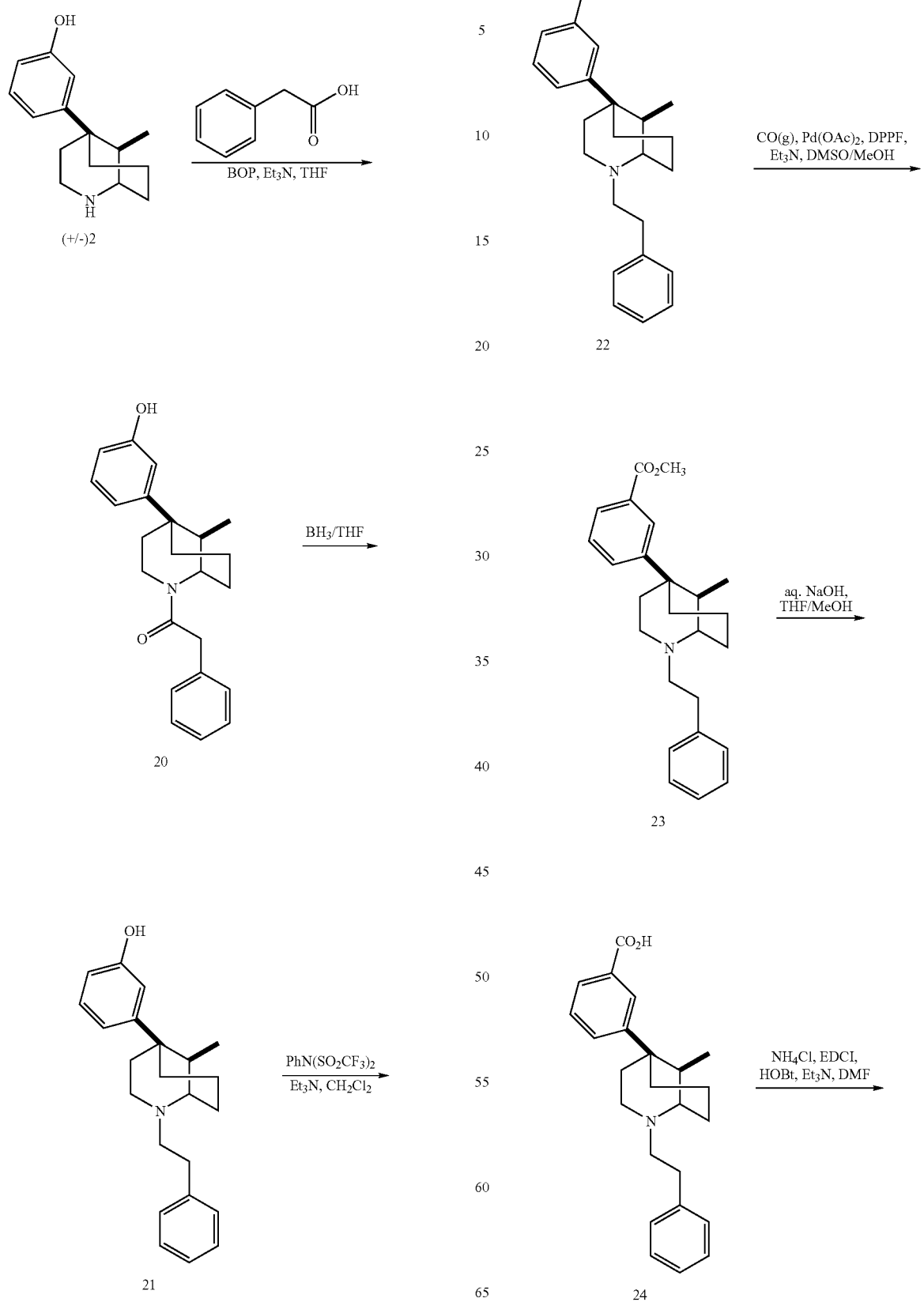

-continued
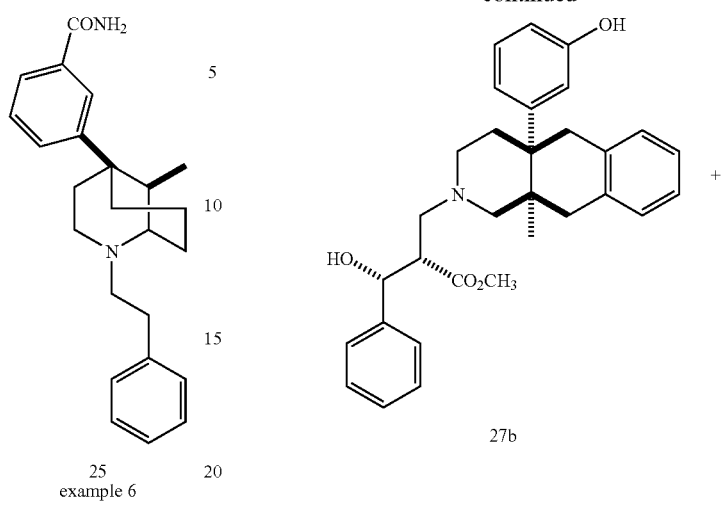
Scheme 4:
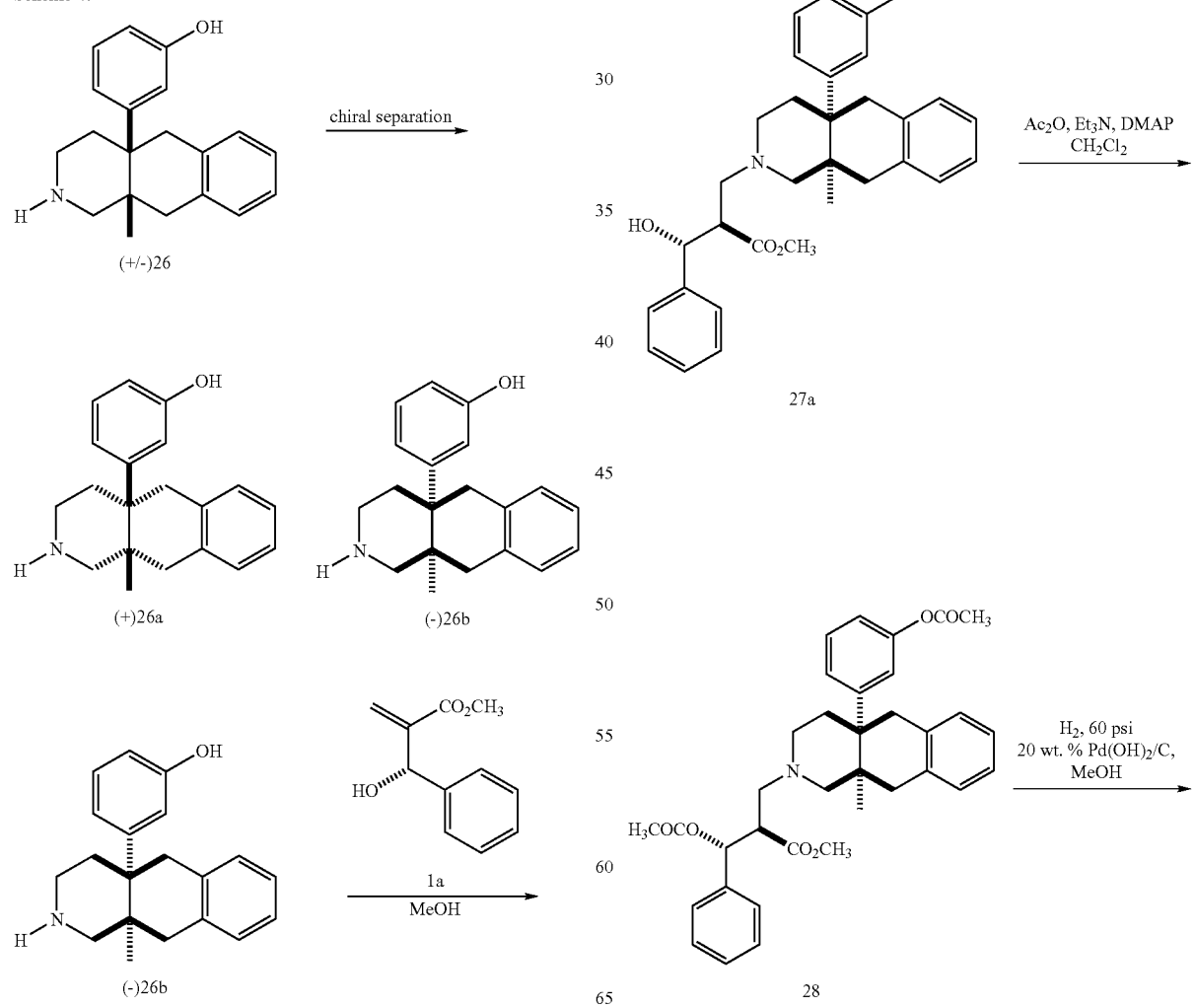

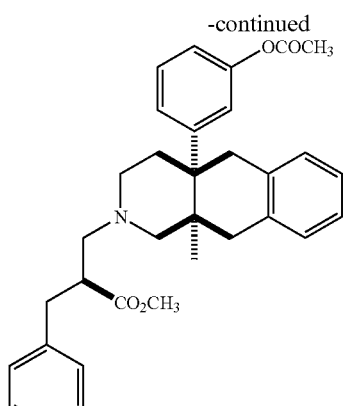
29
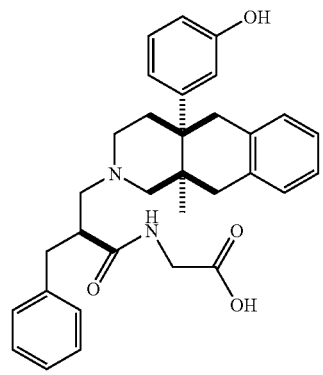
32
example 8
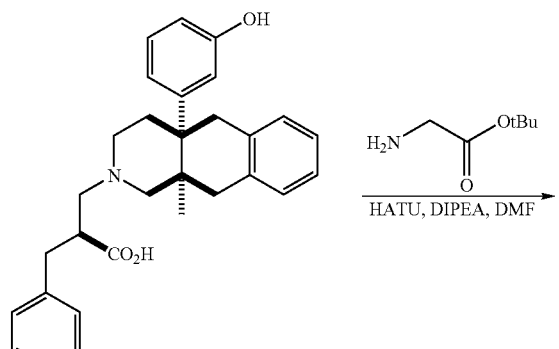
Scheme 5:
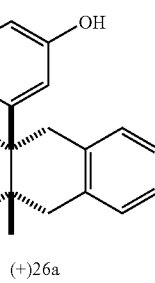
(+)26a
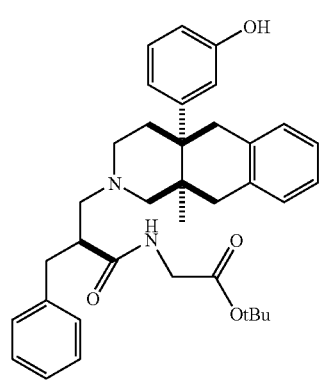
30
example 7
33
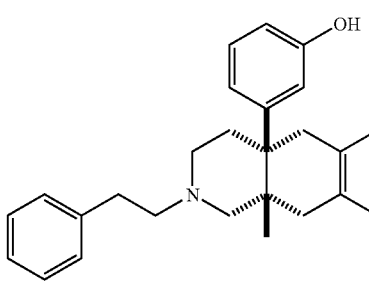
31
34

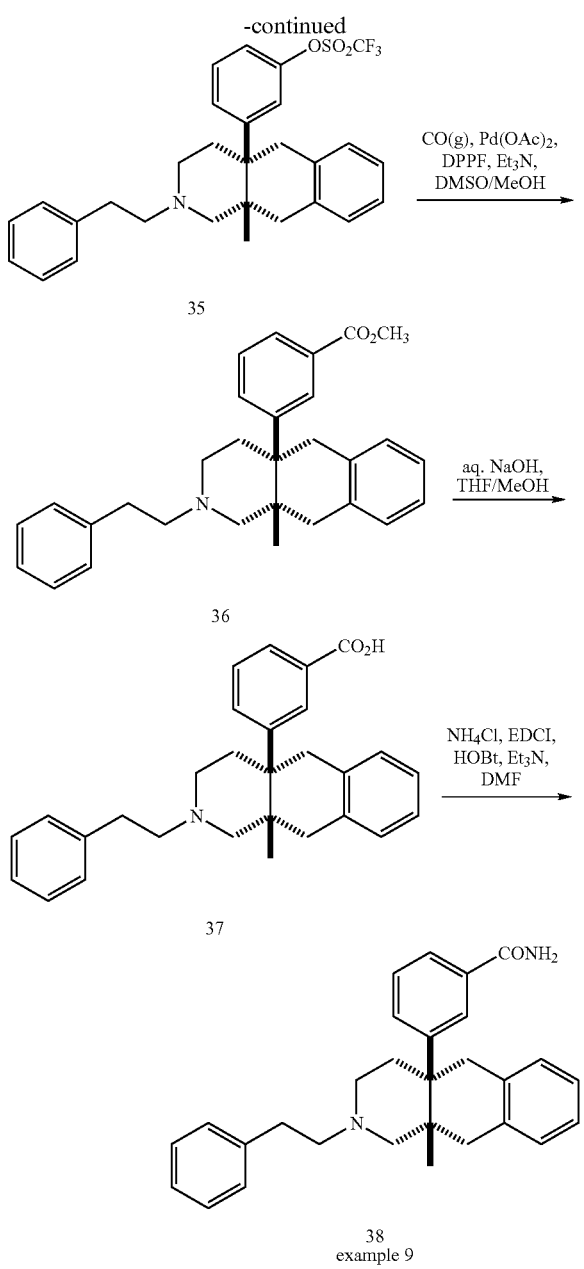

on silica gel glass plates (250 microns) from Analtech and visualized by UV irradiation and iodine. Flash chromatography was conducted with silica gel (200-400 mesh, 60 Å, Aldrich). Chromatographic elution solvent systems are reported as volume: volume ratios. All $^1$H NMR spectra were recorded at ambient temperature on a Bruker-300 MHz spectrometer. They are reported in ppm on the δ scale, from TMS. LC-MS data were obtained using a LC Thermo Finnigan Surveyor-MS Thermo Finnigan AQA in either positive mode or negative mode. Solvent A: 10 mM ammonium acetate, pH 4.5; solvent B: acetonitrile; solvent C: methanol; solvent D: water; column Waters Xterra C18 MS 2.0×50 mm, detector: PDA λ=220-300 nM. Gradient program (positive mode): t=0.00, 600 μL/min, 99% A-1% B; t=0.30, 600 μL/min, 99% A-1% B; t=5.00, 600 μL/min, 1% A-99% B; t=5.30, 600 μL/min, 1% A-99% B. Gradient program (negative mode): t=0.00, 600 μL/min, 9% A-1% B-90% D; t=0.30, 600 μL/min, 9% A-1% B-90% D; t=5.00, 600 μL/min, 99% B-1% D; t=5.30, 600 μL/min, 99% B-1% D.

Example 1

2(S)-Benzyl-3-[5-(3-hydroxy-phenyl)-9-methyl-2-aza-bicyclo[3.3.1]non-2-yl]-propionic acid (6)

(±)Methyl 3-hydroxy-2-methylene-3-phenylpropanoate (1)

Diazabicyclo[2.2.2]octane (5.2 g, 0.046 mol, 0.15 eq) was added to a mixture of benzaldehyde (31.5 mL, 0.309 mol, 1 eq) and methyl acrylate (42 mL, 0.464 mol, 1.5 eq). The reaction mixture was then allowed to stir at room temperature for 7 days. The reaction mixture was purified by column chromatography (eluent: hexane/ethyl acetate=95:5) to give the desired product as colorless oil (42 g, 77%). $R_f$ 0.5 (hexane/ethyl acetate=7:3). $^1$H NMR δ (DMSO-$d_6$) 3.6 (s, 3H), 5.43 (m, 1H), 5.73 (m, 1H), 5.98 (s, 1H), 6.19 (s, 1H), 7.29 (m, 5H).

Preparative Chromatographic Enantioresolution of 1:

Chiral separation: Chiralpak AS; 80% heptane (Fisher 012783), 20% isopropanol (Fisher 010923); 0.75 mL/min; room temperature; 20 μL injection; UV 210 nM.

(+)Methyl 3(S)-hydroxy-2-methylene-3-phenylpropanoate (1a)

$R_f$ 0.5 (hexane/ethyl acetate=7:3). $^1$H NMR δ (DMSO-$d_6$) 3.6 (s, 3H), 5.43 (m, 1H), 5.73 (m, 1H), 5.98 (s, 1H), 6.19 (s, 1H), 7.29 (m, 5H). Fraction 2, $t_R$=8.86 min, 98.8% ee. m.p 48° C. $[\alpha]_D^{25}$=+107.5 (c. 0.01, MeOH).

(−)Methyl 3-hydroxy-2-methylene-3-phenylpropanoate (1b)

$R_f$ 0.5, hexane/ethyl acetate=7:3. $^1$H NMR δ (DMSO-$d_6$) 3.6 (s, 3H), 5.43 (m, 1H), 5.73 (m, 1H), 5.98 (s, 1H), 6.19 (s, 1H), 7.29 (m, 5H). Fraction 1, $t_R$=6.46 min, 99.8% ee. m.p 51° C. $[\alpha]_D^{25}$ (1b)=−113.7 (c. 0.01, MeOH).

Preparative Chromatographic Enantioresolution of 2:

Chiral separation: Chiralcel OD 4.6×250 mm, 5μ; mobile phase: 75% heptane (Fisher 012783), 25% isopropanol (Fisher 010923) w/0.1% TFA; room temperature; 20 μL injection; flow: 0.8 mL/min UV 254 nM.

The present invention will now be illustrated by reference to the following specific, non-limiting examples. Those skilled in the art of organic synthesis may be aware of still other synthetic routes to the invention compounds. The reagents and intermediates used herein are either commercially available or prepared according to standard literature procedures.

EXAMPLES

Synthesis of Compounds

Materials:
All chemicals were reagent grade, purchased from Aldrich Chemical Company, Milwaukee, Wis. or Lancaster Synthesis, Windham, N.H. and used without further purification. Analytical thin-layer chromatography (TLC) was performed (+) 3-(9β-methyl-2-azabicyclo[3.3.1]-non-5-yl)-phenol (2a):

Fraction 2, $t_R$=22.05 min, 99.8% ee. $[\alpha]_D^{25}$ (2a)=+65.21 (c. 0.005, DMSO)

(−) 3-(9β-methyl-2-azabicyclo[3.3.1]-non-5-yl)-phenol (2b)

Fraction 1, $t_R$=14.00 min, 99.8% ee.

A solution of 1a (0.249 g, 1.296 mmol, 1.2 eq) in methanol (0.5 mL) was added drop wise to a solution of 2a (0.250 g, 1.08 mmol, 1 eq) in methanol (1 mL). The mixture was stirred at room temperature under argon for 36 h. The solvent was evaporated and the crude product was purified by column chromatography (eluent: dichloromethane/methanol=99:1). The major diastereoisomer 3a was isolated (0.202 g, 37%); [M+H]+ 424.

Acetic anhydride (118 μL, 1.18 mmol, 2.5 eq) was added dropwise to a cold (0° C.) solution of 3a (0.200 g, 0.472 mmol, 1 eq), triethylamine (165 μL, 1.18 mmol; 2.5 eq) and 4-dimethylaminopyridine (0.0125 g, 0.10 mmol, 0.2 eq) in anhydrous dichloromethane (3 mL). The mixture was stirred under argon at 0° C. for 2 hours. An aqueous saturated solution of sodium bicarbonate (20 mL) was added to the reaction mixture. The organic phase was separated, washed with brine (20 mL) and dried over sodium sulfate. Evaporation of the solvent afforded the crude diacetylated product 4 (0.254 g, 100%) used for the next step without further purification.

A solution of 4 (0.272 g, 0.472 mmol) in methanol (40 mL) was hydrogenated at 60 psi for 16 hours in the presence of Pd(OH)$_2$ (0.120 g) [20 wt. % Pd (dry basis) on carbon wet]. The mixture was filtered through celite and the celite was washed with methanol. The filtrate was concentrated under vacuum. Ethyl acetate (50 mL) was added and the organic solution was washed with an aqueous saturated solution of sodium bicarbonate (150 mL). The organic solution was separated, washed with brine (50 mL) and dried over sodium sulfate. Evaporation of the solvent afforded the crude product 5 used for the next step without further purification (0.200 g, 95%).

A 1N aqueous solution of sodium hydroxide (6 mL, 0.006 mol) was added to a solution of 5 (0.270 g, 0.600 mmol, 1 eq) in THF (6 mL). The mixture was stirred at room temperature for 16 hours. The mixture was then acidified to pH 6 using acetic acid. The mixture was concentrated in vacuo. The crude product 6 (Example 1) was freeze dried and used for the next step without further purification. [M+H]+ 394.

Example 2

{2S-Benzyl-3-[5-(3-hydroxy-phenyl)-9-methyl-2-aza-bicyclo[3.3.1]non-2-yl]-propionylamino}-acetic acid (8)

To a cold (0° C.) solution of glycine tert-butyl ester hydrochloride (0.075 g, 0.450 mmol, 1.5 eq) in anhydrous dimethylformamide (5 mL) was added successively diisopropylethylamine (0.27 mL, 1.5 mmol, 5 eq) and a solution of 6 (0.300 mmol, 1 eq) in anhydrous dimethylformamide (2 mL). To this stirred solution was added under argon a solution of O-(7-azabenzotriazol-1-yl)-N,N,N',N'-tetramethyluronium hexafluorophosphate (HATU) (0.170 g, 0.450 mmol, 1.5 eq) in anhydrous dimethylformamide (1 mL). A further amount of HATU (0.129 g, 0.075 mmol, 0.25 eq) and diisopropylethylamine (55 μL, 0.3 mmol, 1 eq) were added and stirring was continued for a further 5 hours at room temperature. The mixture was concentrated in vacuo. The residue was partitioned between an aqueous saturated solution of sodium bicarbonate (50 mL) and chloroform (50 mL). The organic phase was washed with brine, dried over sodium sulfate, filtered and concentrated. The crude product 7 was purified by column chromatography (eluent: dichloromethane/methanol=99:1) (0.086 g, 57%); [M+H]+ 507.

To a stirred solution of 7 (0.143 g, 0.282 mmol, 1 eq) in dioxane (3 mL) was added a solution of a 4N aqueous solution of HCl (3 mL) drop wise followed by a 1N aqueous solution of HCl (1 mL). The solution was stirred at room temperature for 16 hours. A 12N aqueous solution of HCl (1 mL) was added to the reaction mixture, which was stirred for an additional 4 hours at room temperature. The mixture was concentrated in vacuo. The crude product 8 (Example 2) was purified by preparative HPLC [Genesis C18 column (Jones Chromatography), eluent: 10-50% acetonitrile in water (+0.1% TFA), $t_R$=23 min] (0.091 g, 60%); [M+H]+ 451.

Example 3 and 4

2(S)-Benzyl-3-[5-(3-ethylamino-phenyl)-9-methyl-2-aza-bicyclo[3.3.1]non-2-yl]propan-1-ol (17, Example 3) and 2R-Benzyl-3-[5-(3-ethylamino-phenyl)-9-methyl-2-aza-bicyclo[3.3.1]non-2-yl]propan-1-ol (18, Example 4)

A solution of benzylmalonic acid (20.0 g, 0.103 mol, 1 eq) and paraformaldehyde (4.94 g, 0.164 mol, 1.6 eq) in ethyl acetate (150 mL) was cooled (0° C.) and treated with diethylamine (10.65 mL, 0.103 mol, 1 eq) drop wise, keeping the reaction temperature below 20° C. The reaction was then warmed to reflux for 90 minutes and cooled again on ice. The homogeneous solution was treated with water (20 mL) and concentrated aqueous HCl (12N) (9.0 mL, 0.108 mol) drop wise, keeping the reaction temperature below 10° C. The phases were then separated. The organic layer was washed with brine (100 mL), dried over sodium sulfate, filtered, and the filtrate concentrated under vacuum giving 2-methylene-3-phenylpropanoic acid (10) as a white solid (15 g, 90%).

A solution of 10 (10.3 g, 63.5 mmol) in methanol (100 mL) was cooled on ice and treated dropwise with thionyl chloride (14.0 mL, 192 mmol). After warming to ambient temperature, the reaction was stirred for 18 hours at room temperature and concentrated in vacuo. The crude product was dissolved in diethyl ether, washed with a saturated aqueous solution of sodium bicarbonate and brine, dried over sodium sulfate, filtered, and the filtrate concentrated in vacuo providing the methyl ester 11 (11.2 g, 100%) as a pale yellow oil.

To a solution of (+/−)2 (2 g, 8.643 mmol, 1 eq), 2-benzylacrylic methyl ester 11 (3.19 g, 0.0182 mol, 2.1 eq) in methanol (25 mL) was added triethylamine (3.54 mL, 25.93 mmol, 3 eq) and the solution was heated to reflux for 16 hours under argon. The reaction mixture was concentrated in vacuo, then dissolved in ethyl acetate (200 mL). The mixture was extracted with a 1N aqueous solution of hydrochloric acid (2×200 mL). The combined aqueous phase was alkalinized to pH 8 with solid sodium hydrogenocarbonate, then extracted with ethyl acetate (3×150 mL). The combined organic extracts were dried (sodium sulfate), filtered and concentrated in vacuo to afford a clear tan oil. This oil was purified by column chromatography (eluent: dichloromethane/methanol=98:2) affording the desired compound 12 (mixture of diastereoisomers) (1.07 g, 30.5%).

To a stirred solution of 12 (0.265 g, 0.650 mmol, 1 eq) in anhydrous dichloromethane (3 mL) was added triethylamine (154 μL, 11.05 mmol, 1.7 eq), followed by drop wise addition of a solution of N-phenyltrifluoromethanesulfonimide (0.347 g, 0.975 mmol, 1.5 eq) in anhydrous dichloromethane (0.5 mL) at room temperature under argon. The reaction mixture was allowed to stir for 1 h at room temperature. Dichloromethane (20 mL) was added to the mixture, which was washed with a 1N aqueous solution of sodium hydroxide (20 mL) and brine (20 mL). The organic layer was then dried (sodium sulfate), filtered, and concentrated in vacuo. The crude product was purified by column chromatography (eluent: dichloromethane) affording the desired compound 13 (mixture of diastereoisomers) (0.281 g, 80%).

A mixture of triflate 13 (0.500 g, 0.927 mmol, 1 eq), diphenylphosphinoferrocene (DPPF) (77 mg, 15 mol %, 0.139 mmol), $Pd_2(dba)_3$ (42.5 mg, 5 mol %), sodium tert-butoxide (0.196 g, 2.04 mmol, 2.2 eq) and benzophenone imine (187 µL, 1.112 mmol, 1.2 eq) in anhydrous toluene (40 mL) was degassed using vacuum and argon. The mixture was then heated to 80° C. for 16 hours. The reaction mixture was cooled to room temperature and quenched by addition of an aqueous saturated solution of ammonium chloride (100 mL). The organic layer was separated. The aqueous layer was further extracted with dichloromethane (2×100 mL) and the combined organic extracts were washed with brine (100 mL) prior to drying with sodium sulfate, filtering, and concentration in vacuo. The crude imine 14 was used for the next step without further purification (0.460 g, 85%).

A mixture of the crude imine 14 (0.4 g, 0.682 mmol, 1 eq), hydroxylamine hydrochloride (96.5 mg, 1.365 mmol, 2 eq), sodium acetate (282 mg, 3.425 mmol, 5 eq) in methanol (10 mL) was stirred at room temperature for 45 minutes. The reaction mixture was concentrated in vacuo and partitioned between dichloromethane (3×50 mL) and water (50 mL). The combined organic extracts were washed with brine (50 mL) and dried over sodium sulfate. The organic extracts were filtered and concentrated in vacuo. The crude product was purified by column chromatography (eluent: dichloromethane/methanol=99:1) affording the desired compound 15 (mixture of diastereoisomers) (0.295 g, 100%).

To a cooled (0° C.), stirred solution of the aniline derivative 15 (0.200 g, 0.492 mmol, 1 eq) and triethylamine (135 µL, 0.983 mmol, 2 eq) in anhydrous dichloromethane (10 mL) was added drop wise acetyl chloride (55 µL, 0.738 mmol, 1.5 eq). The mixture was stirred for 1 hour at room temperature and washed with an aqueous saturated solution of sodium hydrogenocarbonate. The aqueous layer was further extracted with dichloromethane (2×25 mL). The combined organic extracts were washed with brine (50 mL), then dried (sodium sulfate) prior to filtration and concentration in vacuo. The crude product was purified by column chromatography (eluent: dichloromethane/methanol=99.5:0.5) affording the desired compound 16 (mixture of diastereoisomers) (0.136 g, 69%).

The acetamide 16 (0.130 g, 0.289 mmol, 1 eq) was dissolved in anhydrous tetrahydrofuran. The solution was cooled (0° C.) and treated with a solution of borane in tetrahydrofuran (0.7225 mmol, 2.5 eq). The reaction mixture was refluxed for 2 hours. The reaction mixture was cooled to room temperature and then quenched by addition of methanol (1 mL). The mixture was heated to reflux for 15 min, cooled to room temperature and partitioned between dichloromethane (3×25 mL) and an aqueous saturated solution of sodium hydrogenocarbonate (25 mL). The combined organic layers were further washed with brine (25 mL) prior to drying (sodium sulfate), filtration and concentration in vacuo. The crude product was purified by column chromatography (eluent: dichloromethane/methanol=98:2) affording the desired compounds 17 (Example 3) (38 mg, 32%) ($[M+H]^+$ 407) and 18 (Example 4) (24 mg, 20%) ($[M+H]^+$ 407).

Example 5

3-[5-(3-amino-phenyl)-9-methyl-2-aza-bicyclo[3.3.1]non-2-yl]-2-benzyl-propionic acid (19)

A solution of 15 (0.275 g, 0.676 mmol, 1 eq) in dioxane (2 mL) was treated with a 4N solution of hydrochloric acid in dioxane (2 mL), followed by a 1N aqueous solution of hydrochloric acid (1 mL). The reaction mixture was stirred at room temperature for 16 hours. A 12N aqueous solution of hydrochloric acid (1 mL) was then added to the mixture, which was stirred for an additional 16 hours at room temperature. The mixture was then concentrated in vacuo and freeze-dried. The crude residue was purified using routine HPLC (eluent: increasing polarity from acetonitrile/water 90:10 to 50:50+ 0.1% trifluoroacetic acid) affording the desired product 19 (Example 5) isolated as its TFA salt; (0.165 g; 50%); $[M+H]^+$ 393.

Example 6

3-[9-methyl-2-phenylethyl-2-aza-bicyclo[3.3.1]non-5-yl]-benzamide (25)

To a solution of (+/−)2 (1.45 g, 6.3 mmol, 1 eq), BOP reagent (2.78 g, 6.3 mmol, 1 eq) and triethylamine (1.9 g, 18.9 mmol, 3 eq) in THF (50 mL) was added phenylacetic acid (1.028 g, 7.56 mmol, 1.2 eq). The mixture was stirred at room temperature overnight. The reaction mixture was then diluted with water (100 mL) and ethyl acetate (150 mL). The organic layer was collected and the aqueous layer was further extracted with ethyl acetate (3×100 mL). The combined organic extracts were washed with an aqueous saturated solution of sodium hydrogenocarbonate, brine and dried over sodium sulfate. After filtration and evaporation of the solvent, the purification by flash chromatography on silica gel (eluent: hexane/ethyl acetate 8:2) afforded the desired product 20 (1.59 g, 72%) as a white solid.

The amide 20 (1.10 g, 3.15 mmol, 1 eq) was dissolved in THF (20 mL). The solution was cooled to 0° C. and borane/dimethyl sulfide complex (2M solution in THF, 3.15 mL, 6.30 mmol, 2 eq) was added drop wise. The resulting mixture was heated to reflux for 3 hours. The mixture was cooled to 0° C. and methanol (10 mL) was added drop wise. The mixture was stirred at room temperature for 1 hour. An anhydrous solution of HCl in ether (2M solution, 5 mL) was added to the mixture, which was refluxed for 1 hour. The mixture was cooled to 0° C. and an additional amount of methanol (10 mL) was added. After removal of the solvent, the mixture was made basic (pH 12) using a 1N aqueous solution of sodium hydroxide and extracted with ethyl acetate (3×50 mL). The combined organic extracts were dried over magnesium sulfate and concentrated under reduced pressure affording the amine 21 (0.79 g, 75%) used for the next step without further purification.

To a cold (0° C.) suspension of 21 (0.745 g, 2.22 mmol, 1 eq) in anhydrous dichloromethane (20 mL) was added N-phenyltrifluoromethanesulfonimide (0.872 g, 2.442 mmol, 1.1 eq) followed by addition of triethylamine (0.533 g, 2.4 eq). The mixture was stirred at room temperature overnight. The mixture was then washed with water (20 mL), a 1N aqueous solution of sodium hydroxide (10 mL), water (20 mL) and brine (15 mL). The organic phase was dried over magnesium sulfate and concentrated to furnish the crude product. Purification of the crude product by column chromatography on silica gel (eluent: hexane/ethyl acetate 95:5) afforded the desired triflate 22 (1.168 g, 100%).

To a stirred solution of 22 (1.15 g, 2.46 mmol, 1 eq) in a mixture methanol (10 mL) and DMSO (12 mL) was added triethylamine (0.546 g, 5.41 mmol, 2 eq). Carbon monoxide gas was bubbled through the mixture for 5 min. To the mixture was added palladium (II) acetate (55 mg, 0.246 mmol, 0.1 eq) followed by DPPF (272 mg, 0.2 eq). Carbon monoxide gas was bubbled through the mixture for 15 minutes and stirring was continued under an atmosphere of CO at 65° C. overnight. The mixture was then cooled to room temperature and poured into water (100 mL). The mixture was extracted with ethyl acetate (3×30 mL). The combined organic extracts were washed with water (20 mL), brine (20 mL), and dried over magnesium sulfate. Evaporation of the solvent afforded a dark oil. The crude product was purified by column chromatography (eluent hexane/ethyl acetate 95:5) affording the desired compound 23 (0.112 g, 12%).

A 1N aqueous solution of sodium hydroxide (2 mL) was added to a solution of 23 (0.105 g, 0.278 mmol, 1 eq) in THF (5 mL) and methanol (2 mL). The mixture was stirred at room temperature overnight. The mixture was cooled to 0° C. and 2 mL of a 2N anhydrous solution of hydrochloric acid in diethyl ether was added. The mixture was concentrated under reduced pressure. The desired compound 24 was obtained as a white solid (85 mg, 84%).

To a suspension of 24 (74 mg, 0.20 mmol, 1 eq) and triethylamine (61 mg, 0.6 mmol, 3 eq) in dimethylformamide (5 mL) was added ammonium chloride (54 mg, 1 mmol, 5 eq), 1-hydroxybenzotriazole (HOBt) (32 mg, 0.24 mmol, 1.2 eq) and EDCI (15 mg, 0.28 mmol, 1.4 eq) and the mixture was stirred for 24 hours at room temperature. The mixture was poured into an aqueous saturated solution of sodium carbonate and extracted with ethyl acetate. The organic layer was separated, washed with water, dried over magnesium sulfate, filtered and concentrated. The crude product was purified by column chromatography (eluent: dichloromethane/methanol 95:5) affording the desired compound 25 (Example 6) (50 mg, 69%): m/z 363 (M+H$^+$).

Example 7

2-Benzyl-3-[4a-(3-hydroxy-phenyl)-10a-methyl-3,4, 4a,5,10,10a-hexahydro-1H-benzo[g]isoquinolin-2-yl]-propionic acid (30)

Preparative Chromatographic Enantioresolution of 26:

Chiral separation: Chiralpak AD 4.6×250 mm, 5µ; mobile phase: 85% heptane (Fisher 012783), 15% isopropanol (Fisher 010923) w/0.1% TFA; room temperature; 20 µL injection; flow: 0.8 mL/min; UV 254 nM.

(−) 1,2,3,4,4a,5,10,10a-Octahydro-4a-(3-hydroxyphenyl)-10a-methyl-2-benzo[g]isoquinoline (26b)

Fraction 2, $t_R$=8.20 min, 99.9% ee. $[\alpha]_D^{25}$ (26b)=−28.59 (c. 0.005, DMSO)

(+) 1,2,3,4,4a,5,10,10a-Octahydro-4a-(3-hydroxyphenyl)-10a-methyl-2-benzo[g]isoquinoline (26a)

Fraction 1, $t_R$=1.66 min, 99.7% ee. $[\alpha]_D^{25}$ (26a)=+34.47 (c. 0.005, DMSO)

A solution of 1a (0.394 g; 2.05 mmol; 1.2 eq) in methanol (1 mL) was added drop wise to a suspension of (−)(26b) (0.5 g, 1.704 mmol, 1 eq) in methanol (5 mL). The mixture was stirred at room temperature under argon for 72 h. The solvent was evaporated and the crude product was purified by column chromatography (eluent: diethyl ether/petroleum ether mixture of increasing polarity=25/75 to 40/60). The major diastereoisomer 27a was isolated (0.562 g, 68%); [M+H]$^+$ 486.

Acetic anhydride (203 µL, 2.03 mmol, 2.5 eq) was added drop wise to a cold (0° C.) solution of 27a (0.462 g, 0.811 mmol, 1 eq), triethylamine (285 µL, 2.03 mol; 2.5 eq) and 4-dimethylaminopyridine (0.020 g, 0.162 mmol; 0.2 eq) in anhydrous dichloromethane (5 mL). The mixture was stirred under argon at 0° C. for 3 hours. An aqueous saturated solution of sodium bicarbonate (25 mL) was added to the reaction mixture. The organic phase was separated, washed with brine (25 mL) and dried over sodium sulfate. Evaporation of the solvent afforded the crude diacetylated product 28 (0.5 g, 100%) used for the next step without further purification.

A solution of 28 (0.5 g, 0.211 mmol) in methanol (15 mL) was hydrogenated at 60 psi for 16 hours in the presence of Pd(OH)$_2$ (0.250 g) [20 weight % Pd (dry basis) on carbon wet]. Further catalyst (0.200 g) was added to the mixture, which was hydrogenated at 60 psi for an additional 4 hours. The mixture was filtered through celite and the celite was washed with methanol. The filtrate was concentrated under vacuum. Ethyl acetate (50 mL) was added and the organic solution was washed with an aqueous saturated solution of sodium bicarbonate (150 mL). The organic solution was separated, washed with brine (50 mL) and dried over sodium sulfate. Evaporation of the solvent afforded the crude product 29 used for the next step without further purification (0.220 g, 54%).

A 1N aqueous solution of sodium hydroxide (3 mL) was added to a solution of 29 (0.200 g, 0.391 mmol, 1 eq) in THF (3 mL). The mixture was stirred at room temperature for 16 hours. The mixture was then acidified to pH 6 using a 1N aqueous solution of HCl. A white precipitate was formed. The precipitate was collected by filtration, washed with ice cold water (0-5° C.) and ether providing the title compound 30 (Example 7) (0.132 g, 74%); [M+H]$^+$ 456.

Example 8

{2-Benzyl-3-[4a-(3-hydroxy-phenyl)-10a-methyl-3, 4,4a,5,10,10a-hexahydro-1H-benzo[g]isoquinolin-2-yl]-propionylamino}-acetic acid (32)

To a cold (0° C.) solution of glycine tert-butyl ester hydrochloride (0.050 g, 0.296 mmol, 1.5 eq) in anhydrous dimethylformamide (5 mL) was added successively diisopropylethylamine (0.18 mL, 1 mmol, 5 eq) and a solution of 30 (0.090 g, 0.198 mmol, 1 eq) in anhydrous dimethylformamide (1 mL). To this stirred solution was added under argon a solution of O-(7-azabenzotriazol-1-yl)-N,N,N',N'-tetramethyluronium hexafluorophosphate (HATU) (0.112 g, 0.296 mmol, 1.5 eq) in anhydrous dimethylformamide (1 mL). The mixture was stirred at room temperature under argon for 16 hours and concentrated in vacuo. The residue was partitioned between an aqueous saturated solution of sodium bicarbonate (30 mL) and chloroform (30 mL). The aqueous layer was further extracted with chloroform (30 mL) and the combined organic extracts were washed with brine, dried over sodium sulfate, filtered, and concentrated. The crude product was purified by column chromatography (eluent: dichloromethane/methanol=99:1) affording the desired t-butyl ester 31 (0.103 g, 91%); [M+H]$^+$ 569.

To a stirred solution of 31 (0.093 g, 0.181 mmol, 1 eq) in dioxane (2.5 mL) was added a solution of a 4N aqueous solution of HCl (2.5 mL) drop wise. A white precipitate formed after 20 minutes. To the suspension was added a 1N aqueous solution of HCl (1 mL). The clear solution was stirred at room temperature for 16 hours. A 12N aqueous solution of HCl (1 mL) was added to the reaction mixture, which was stirred for an additional 16 hours at room temperature. The mixture was concentrated in vacuo. The crude product was purified by preparative HPLC [Genesis C18 column (Jones Chromatography), eluent: 10-50% acetonitrile in water (+0.1% TFA), $t_R$=30 min)] affording the title compound 32 (Example 8) (0.064 g, 58%); [M+H]$^+$ 513.

Example 9

3-(10a-Methyl-2-phenethyl-1,3,4,5,10,10a-hexahydro-2H-benzo[g]isoquinolin-4a-yl)-benzamide (38)

To a solution of (+)26a (0.483 g, 1.65 mmol, 1 eq), BOP reagent (0.73 g, 1.65 mmol, 1 eq) and triethylamine (0.5 g, 4.95 mmol, 3 eq) in THF (20 mL) was added phenylacetic acid (0.269 g, 1.98 mmol, 1.2 eq). The mixture was stirred at room temperature for 1 hour. The reaction mixture was then diluted with water (100 mL) and ethyl acetate (150 mL). The organic layer was collected and the aqueous layer was further extracted with ethyl acetate (3×100 mL). The combined organic extracts were washed with an aqueous saturated solution of sodium hydrogenocarbonate, brine and dried over sodium sulfate. After filtration and evaporation of the solvent, the crude product 33 was obtained (0.5 g, 73%).

The crude amide 33 obtained previously (0.480 g, 1.166 mmol, 1 eq) was dissolved in THF (20 mL). The solution was cooled to 0° C. and borane/dimethyl sulfide complex (2M solution in THF, 1.16 mL, 2.332 mmol, 2 eq) was added drop wise. The resulting mixture was heated to reflux for 4 hours. The mixture was cooled to 0° C. and methanol (10 mL) was added drop wise. The mixture was stirred at room temperature for 1 hour. Anhydrous HCl in ether (2M solution, 5 mL) was added to the mixture, which was gently refluxed for 1 hour. The mixture was cooled to 0° C. and an additional amount of methanol (10 mL) was added. After removal of the solvent, the mixture was made basic (pH 12) using a 1N aqueous solution of sodium hydroxide and extracted with diethyl ether (3×50 mL). The combined organic extracts were dried over magnesium sulfate and concentrated under reduced pressure affording the crude product. Purification of the crude product by column chromatography (eluent: dichloromethane/methanol 97:3) gave the desired amine 34 (0.38 g, 81%) as a white solid.

To a cold (0° C.) suspension of 34 (0.350 g, 0.88 mmol, 1 eq) in anhydrous dichloromethane (20 mL) was added N-phenyltrifluoromethanesulfonimide (0.346 g, 0.968 mmol, 1.1 eq), followed by addition of triethylamine (0.239 g, 2.4 eq). The mixture was stirred at room temperature overnight. The mixture was then washed with water (20 mL), a 1N aqueous solution of sodium hydroxide (10 mL), water (20 mL) and brine (15 mL). The organic phase was dried over magnesium sulfate and concentrated to furnish the crude product. Purification of the crude product by column chromatography on silica gel (eluent: hexane/ethyl acetate 95:5) afforded the desired triflate 35 (0.420 g, 90%).

To a stirred solution 35 (0.400 g, 0.756 mmol, 1 eq) in a mixture methanol (10 mL) and DMSO (12 mL) was added triethylamine (0.153 g, 1.512 mmol, 2 eq). Carbon monoxide gas was bubbled through the mixture for 5 minutes. To the mixture was added palladium (II) acetate (17 mg, 0.0756 mmol, 0.1 eq.) followed by DPPF (84 mg, 0.2 eq). Carbon monoxide gas was bubbled through the mixture for 15 minutes and stirring was continued under an atmosphere of CO at 65° C. overnight. The mixture was then cooled to room temperature and poured into water (100 mL). The mixture was extracted with ethyl acetate (3×30 mL). The combined organic extracts were washed with water (20 mL), brine (20 mL), and dried over magnesium sulfate. Evaporation of the solvent afforded a dark oil. The crude product was purified by column chromatography (eluent hexane/ethyl acetate 95:5) affording the desired compound 36 (0.140 g, 42%).

A 1N aqueous solution of sodium hydroxide (2 mL) was added to a solution of 36 (0.116 g, 0.272 mmol, 1 eq) in THF (5 mL) and methanol (2 mL). The mixture was stirred at room temperature for 3 hours. The mixture was cooled to 0° C. and 2 mL of a 2N anhydrous solution of hydrochloric acid in diethyl ether was added. The mixture was concentrated under reduced pressure. The desired compound 37 was obtained as a white solid (118 mg, 100%).

To a suspension of 37 (116 mg, 0.272 mmol, 1 eq) and triethylamine (82 mg, 0.816 mmol, 3 eq) in dimethylformamide (5 mL) was added ammonium chloride (73 mg, 1.360 mmol, 5 eq), HOBt (44 mg, 0.326 mmol, 1.2 eq) and EDCI (73 mg, 0.381 mmol, 1.4 eq) and the mixture was stirred for 24 hours at room temperature. The mixture was poured into an aqueous saturated solution of sodium carbonate and extracted with ethyl acetate. The organic layer was separated, washed with water, dried over magnesium sulfate, filtered, and concentrated. The crude product was purified by column chromatography (eluent: dichloromethane/methanol 95:5) affording the desired compound 38 (Example 9) (85 mg, 73%); [M+H]$^+$ 425

Biological Assays

The potencies of the compounds were determined by testing the ability of a range of concentrations of each to inhibit the binding of the non-selective opioid antagonist, [$^3$H]diprenorphine, to the cloned human μ, κ, and δ opioid receptors, expressed in separate cell lines. IC$_{50}$ values were obtained by nonlinear analysis of the data using GraphPad Prism version 3.00 for Windows (GraphPad Software, San Diego). K$_i$ values were obtained by Cheng-Prusoff corrections of IC$_{50}$ values.

Receptor Binding (In Vitro Assay)

The receptor binding method (DeHaven and DeHaven-Hudkins, 1998) was a modification of the method of Raynor, et al. (1994). After dilution in buffer A and homogenization as before, membrane proteins (10-80 μg) in 250 μL were added to mixtures containing test compound and [$^3$H]diprenorphine (0.5 to 1.0 nM, 40,000 to 50,000 dpm) in 250 μL of buffer A in 96-well deep-well polystyrene titer plates (Beckman). After incubation at room temperature for one hour, the samples were filtered through GF/B filters that had been pre-soaked in a solution of 0.5% (w/v) polyethylenimine and 0.1% (w/v) bovine serum albumin in water. The filters were rinsed 4 times with 1 mL of cold 50 mM Tris HCl, pH 7.8 and radioactivity remaining on the filters determined by scintillation spectroscopy. Nonspecific binding was determined by the minimum values of the titration curves and was confirmed by separate assay wells containing 10 μM naloxone. $K_i$ values were determined by Cheng-Prusoff corrections of $IC_{50}$ values derived from nonlinear regression fits of 12 point titration curves using GraphPad Prism® version 3.00 for Windows (GraphPad Software, San Diego, Calif.).

To determine the equilibrium dissociation constant for the inhibitors ($K_i$), radioligand bound (cpm) in the presence of various concentrations of test compounds was measured. The concentration to give half-maximal inhibition ($EC_{50}$) of radioligand binding was determined from a best nonlinear regression fit to the following equation, $$Y = \text{Bottom} + \frac{(\text{Top} - \text{Bottom})}{1 + 10^{X - Log EC_{50}}}$$

where Y is the amount of radioligand bound at each concentration of test compound, Bottom is the calculated amount of radioligand bound in the presence of an infinite concentration of test compound, Top is the calculated amount of radioligand bound in the absence of test compound, X is the logarithm of the concentration of test compound, and $LogEC_{50}$ is the log of the concentration of test compound where the amount of radioligand bound is half-way between Top and Bottom. The nonlinear regression fit was performed using the program Prism® (GraphPad Software, San Diego, Calif.). The $K_i$ values were then determined from the $EC_{50}$ values by the following equation, $$K_i = \frac{EC_{50}}{1 + \frac{[\text{ligand}]}{K_d}}$$

where [ligand] is the concentration of radioligand and $K_d$ is the equilibrium dissociation constant for the radioligand.

The potencies of the antagonists were assessed by their abilities to inhibit agonist-stimulated [$^{35}$S]GTPγS binding to membranes containing the cloned human μ, κ, or δ opioid receptors. The agonists used were loperamide for the μ opioid receptor, U50488H for the κ opioid receptor, and BW373U86 for the δ opioid receptor.

To determine the $IC_{50}$ value, which was the concentration to give half-maximal inhibition of agonist-stimulated [$^{35}$S]GTPγS binding, the amount of [$^{35}$S]GTPγS bound in the presence of a fixed concentration of agonist and various concentrations of antagonist was measured. The fixed concentration of agonist was the $EC_{80}$ for the agonist, which was the concentration to give 80% of the relative maximum stimulation of [$^{35}$S]GTPγS binding. The $IC_{50}$ value was determined from a best nonlinear regression fit of the data to the following equation, $$Y = \text{Bottom} + \frac{(\text{Top} - \text{Bottom})}{1 + 10^{X - Log IC_{50}}}$$

where Y is the amount of [$^{35}$S]GTPγS bound at each concentration of antagonist, Bottom is the calculated amount of [$^{35}$S]GTPγS bound in the presence of an infinite concentration of antagonist, Top is the calculated amount of [$^{35}$S]GTPγS bound in the absence of added antagonist, X is the logarithm of the concentration of antagonist, and $LogIC_{50}$ is the logarithm of the concentration of antagonist where the amount of [$^{35}$S]GTPγS bound is halfway between Bottom and Top. The nonlinear regression fit was performed using GraphPad Prism® version 3.00 for Windows (GraphPad Software, San Diego, Calif.).

Mouse Gastrointestinal Transit (GIT) Assay (In Vivo Assay)

Male Swiss-Webster mice (25-30 g) obtained from Ace Animals (Boyertown, Pa.) were used for all experiments. Mice were housed 4/cage in polycarbonate cages with food and water available ad libitum. Mice were on a 12 hours light:dark schedule with lights on at 6:30 a.m. All experiments were performed during the light cycle. Mice were fasted the night before the experiment, with water available ad libitum.

Mice were administered vehicle (10% DMSO:20% Cremophor EL:70% saline) or test compound (10 mg/kg) orally 2 or 6 hour before determination of GIT. Compounds were administered in a volume of 0.1 ml/10 g of body weight. Morphine (3 mg/kg) or vehicle (0.9% saline) was administered s.c. 35 minutes prior to determination of GIT. Ten minutes after the morphine treatment, mice were administered 0.2 ml of a charcoal meal orally. The charcoal meal consisted of a slurry of charcoal, flour, and water in the following ratio (1:2:8, w:w:v). Twenty-five minutes after receiving the charcoal meal, the mice were euthanized with $CO_2$ and GIT determined. GIT is expressed as the % GIT by the following formula:

$$\frac{(\text{distance to leading edge of charcoal meal (cm)})}{(\text{total length of the small intestine (cm)})} \times 100$$

For each compound a % Antagonism (% A) value was determined for the 2 and 6 hour antagonist pretreatment. Using the mean % GIT for each treatment group, % A was calculated using the following formula:

$$1 - \frac{((\text{mean vehicle response} - \text{mean antagonist} + \text{morphine response}))}{(\text{mean vehicle response} - \text{mean morphine response})} \times 100$$

TABLE 1

| Example | Name | Structure | [M + H]+ |
|---------|------|-----------|----------|
| 1 | 2(S)-benzyl-3-[5-(3-hydroxy-phenyl)-9-methyl-2-aza-bicyclo[3.3.1]non-2-yl]-propionic acid obtained from (+)2a | 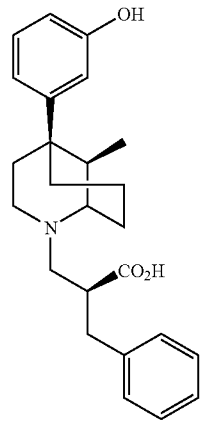 | 394 |
| 2 | {2(S)-benzyl-3-[5-(3-hydroxy-phenyl)-9-methyl-2-aza-bicyclo[3.3.1]non-2-yl]-propionylamino} acetic acid obtained from (+)2a | 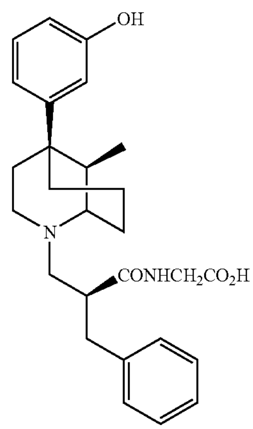 | 451 |
| 3 | 2(S)-benzyl-3-[5-(3-ethylamino-phenyl)-9-methyl-2-aza-bicyclo[3.3.1]non-2-yl]-propan-1-ol obtained from (+/−)2 | 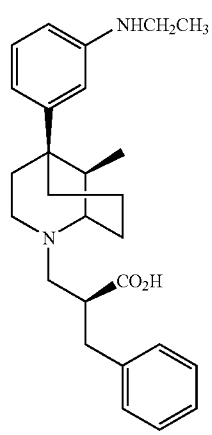 | 407 |

TABLE 1-continued

| Example | Name | Structure | [M + H]+ |
|---|---|---|---|
| 4 | 2(R)-benzyl-3-[5-(3-ethylamino-phenyl)-9-methyl-2-aza-bicyclo[3.3.1]non-2-yl]-propan-1-ol obtained from (+/−)2 | 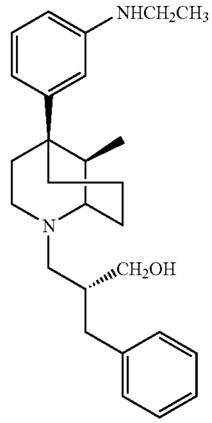 | 407 |
| 5 | 3-[5-(3-amino-phenyl)-9-methyl-2-aza-bicyclo[3.3.1]non-2-yl]-2-benzyl-propionic acid obtained from (+/−)2 | 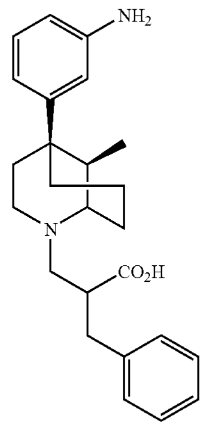 | 393 |
| 6 | 3-[9-Methyl-2-phenylethyl-2-aza-bicyclo[3.3.1]non-5-yl]-benzamide obtained from (+/−)2 | 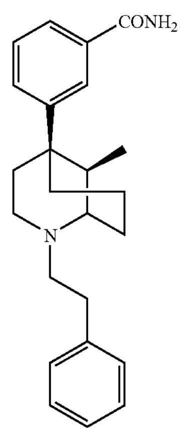 | 363 |

TABLE 1-continued

| Example | Name | Structure | [M + H]+ |
|---------|------|-----------|----------|
| 7 | 2-Benzyl-3-[4a-(3-hydroxy-phenyl)-10a-methyl-3,4,4a,5,10,10a-hexahydro-1H-benzo[g]isoquinolin-2-yl]-propionic acid | 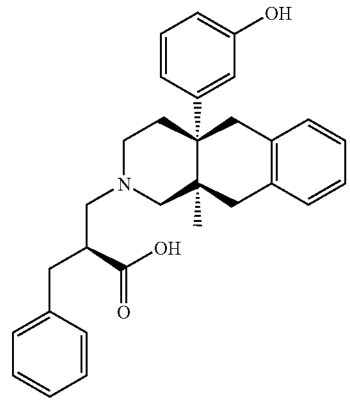 | 456 |
| 8 | {2-Benzyl-3-[4a-(3-hydroxy-phenyl)-10a-methyl-3,4,4a,5,10,10a-hexahydro-1H-benzo[g]isoquinolin-2-yl]-propionylamino}-acetic acid | 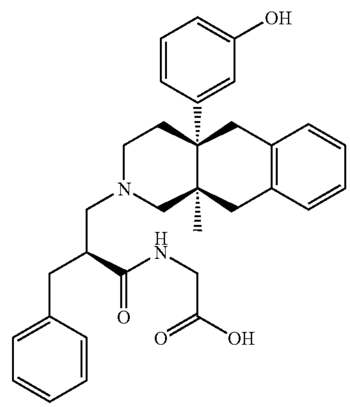 | 513 |
| 9 | 3-(10a-Methyl-2-phenethyl-1,3,4,5,10,10a-hexahydro-2H-benzo[g]isoquinolin-4a-yl)-benzamide | 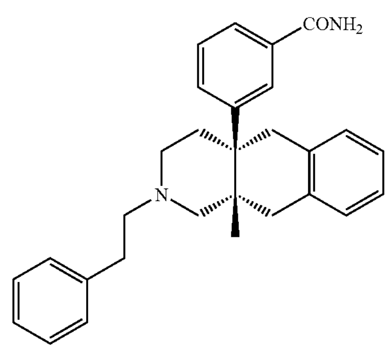 | 425 |

Biological Results

Examples 1-9, listed in Table 1, were tested for their affinity towards the μ, δ and κ opioid receptors. All the ligands tested bind to the human μ opioid receptor with affinity greater than 10,000 nM. These ligands display various degrees of selectivity, e.g., μ vs. δ or μ Vs. κ. The activity of selected ligands was also evaluated in vitro. These compounds were found to be pure antagonist at μ opioid receptor (no agonist activity detectable at concentration >10 μM). For example, ligand example 2 ($K_i$=1.5 nM) was found to possess μ receptor antagonist potency comparable to the μ receptor antagonist potency of Alvimopan ($K_i$=0.5 nM).

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference, in their entirety.

Those skilled in the art will appreciate that numerous changes and modifications can be make to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of formula I:

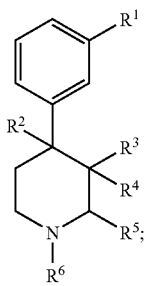

wherein:
R$^1$ is —OR$^7$, —NR$^7$R$^8$, —COOR$^7$, —CONR$^7$R$^8$, or —CH$_2$OH;
each R$^7$ is independently H, alkyl, cycloalkyl, alkylcycloalkyl, or aralkyl;
each R$^8$ is independently H, alkyl, aralkyl, or aryl;
R$^2$ and R$^3$ together with the carbon atoms to which they are attached form a fused carbocycle, R$^4$ is alkyl, and R$^5$ is H;
R$^6$ is H or —(CHR$^9$)$_m$W;
each R$^9$ is independently H, alkyl, cycloalkyl, alkylcycloalkyl, aryl, aralkyl or heteroaryl;
W is H, alkyl, cycloalkyl, alkylcycloalkyl, heterocycloalkyl, alkylheterocycloalkyl, aryl, heteroaryl, —CH$_2$OH, —CH$_2$OR$^7$, or —C(═O)R$^{10}$;
R$^{10}$ is —OR$^7$ or —NR$^7$R$^{11}$;
R$^{11}$ is H, alkyl, aralkyl, aryl or —(CHR$^9$)$_n$C(═O)R$^{12}$;
R$^{12}$ is —OR$^7$ or —NR$^7$R$^8$;
m is an integer from 1 to 4; and
n is an integer from 1 to 4;
provided that:
(1) when R$^1$ is —OCH$_3$, R$^4$ is CH$_3$, R$^5$ is H, and R$^2$ and R$^3$ together with the carbon atoms to which they are attached form unsubstituted tetrahydronaphthalene, then W is other than H, alkyl, or phenyl;
(2) when R$^1$ is —OH, then W is heterocycloalkyl, alkylheterocycloalkyl, —CH$_2$OH, or —C(═O)R$^{10}$; and
(3) when R$^1$ is —OH and W is heterocycloalkyl or alkylheterocycloalkyl in which the heterocyclic ring moiety of the heterocycloalkyl or alkylheterocycloalkyl contains only one heteroatom, wherein the heteroatom is nitrogen, then the heterocyclic ring moiety is connected to —(CHR$^9$)$_m$— through a heterocyclic ring carbon atom;
or a stereoisomer, pharmaceutically acceptable salt, or N-oxide thereof.

2. A compound according to claim 1, wherein R$^1$ is —OR$^7$, —NR$^7$R$^8$, or —CONR$^7$R$^8$.

3. A compound according to claim 2, wherein R$^1$ is —OH, —NHR$^8$, or —CONHR$^8$.

4. A compound according to claim 1, wherein R$^6$ is —(CHR$^9$)$_m$W.

5. A compound according to claim 4, wherein:
R$^6$ is:

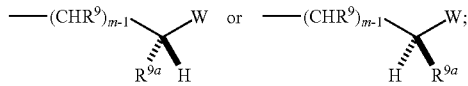

and
R$^{9a}$ is H, alkyl, cycloalkyl, alkylcycloalkyl, aryl, aralkyl or heteroaryl.

6. A compound according to claim 5, wherein:
R$^6$ is:

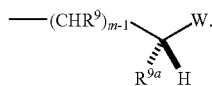

7. A compound according to claim 5, wherein:
R$^6$ is:

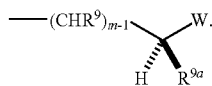

8. A compound according to claim 5, wherein W is aryl, —CH$_2$OH, —CH$_2$OR$^7$, or —C(═O)R$^{10}$.

9. A compound according to claim 8, wherein W is aryl, —CH$_2$OH, or —C(═O)OH.

10. A compound according to claim 8, wherein W is —C(═O)NR$^7$R$^{11}$.

11. A compound according to claim 10, wherein W is —C(═O)NHR$^{11}$.

12. A compound according to claim 11, wherein R$^{11}$ is —(CHR$^9$)$_n$C(═O)R$^{12}$.

13. A compound according to claim 12, wherein R$^{11}$ is —(CHR$^9$)$_n$C(═O)OH.

14. A compound according to claim 1, wherein m is 1 or 2.

15. A compound according to claim 1, wherein n is 1 or 2.

16. A compound according to claim 15, wherein n is 1.

17. A compound according to claim 1, wherein the fused carbocycle is tetrahydroindene, tetrahydronaphthalene, or tetrahydroanthracene.

18. A compound according to claim 17, wherein the fused carbocycle is tetrahydronaphthalene.

19. A compound according to claim 18, of formula IV:

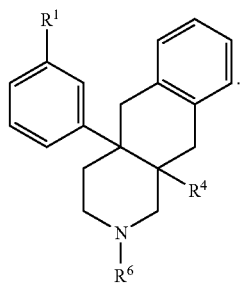

20. A compound according to claim 19, of formula Va or Vb:

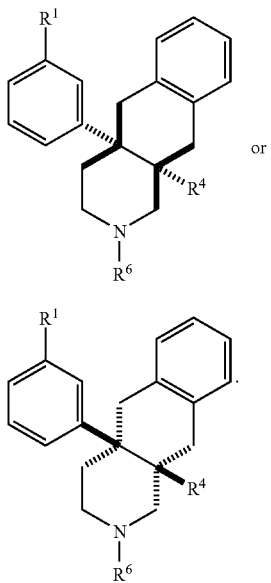

21. A compound according to claim 20, wherein $R^4$ is methyl.

22. A compound according to claim 21, wherein:
$R^6$ is:

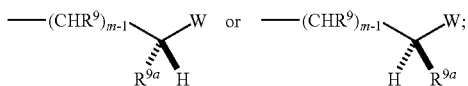

and
$R^{9a}$ is H, alkyl, cycloalkyl, alkylcycloalkyl, aryl, aralkyl or heteroaryl.

23. A compound according to claim 22, wherein:
$R^6$ is:

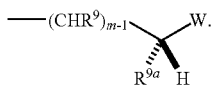

24. A compound according to claim 22, wherein:
$R^6$ is:

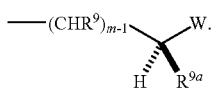

25. A compound according to claim 24, of formula Va, wherein:
$R^1$ and $R^{10}$ are each —$OR^7$;
$R^4$ is methyl;
$R^7$ and $R^9$ are each H;
$R^{9a}$ is benzyl;
W is —$C(=O)R^{10}$; and
m is 2.

26. A compound according to claim 24, of formula Va, wherein:
$R^1$ and $R^{12}$ are each —$OR^7$;
$R^4$ is methyl;
$R^7$ and $R^9$ are each H;
$R^{9a}$ is benzyl;
W is —$C(=O)R^{10}$;
$R^{10}$ is —$NR^7R^{11}$;
$R^{11}$ is —$(CHR^9)_nC(=O)R^{12}$;
n is 1; and
m is 2.

27. A compound according to claim 22, of formula Vb, wherein:
$R^1$ is $C(=O)NR^7R^8$;
$R^4$ is methyl;
$R^7$, $R^8$, $R^9$, and $R^{9a}$ are each H;
W is phenyl; and
m is 2.

28. A compound according to claim 1, wherein the compound is:
2-benzyl-3-[4a-(3-hydroxy-phenyl)-10a-methyl-3,4,4a,5,10,10a-hexahydro-1H-benzo[g]isoquinolin-2-yl]-propionic acid;
{2-benzyl-3-[4a-(3-hydroxy-phenyl)-10a-methyl-3,4,4a,5,10,10a-hexahydro-1H-benzo[g]isoquinolin-2-yl]-propionylamino}-acetic acid; or
3-(10a-methyl-2-phenethyl-1,3,4,5,10,10a-hexahydro-2H-benzo[g]isoquinolin-4-a-yl)-benzamide;
or a stereoisomer thereof.

29. A pharmaceutical composition, comprising:
a pharmaceutically acceptable carrier; and
an effective amount of a compound according to claim 1.

30. A pharmaceutical composition, comprising:
a pharmaceutically acceptable carrier;
an effective amount of at least one opioid; and
an effective amount of a compound according to claim 1.

31. A pharmaceutical composition according to claim 30, wherein the opioid is alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol or mixtures thereof.

32. A method of binding opioid receptors in a patient in need thereof, comprising the step of:
administering to the patient a composition comprising an effective amount of a compound according to claim 1.

33. A method according to claim 32, wherein the compound binds μ opioid receptors.

34. A method according to claim 33, wherein the μ opioid receptors are located in the central nervous system.

35. A method according to claim 33, wherein the μ opioid receptors are located peripherally to the central nervous system.

36. A method according to claim 32, wherein the compound binds κ opioid receptors.

37. A method according to claim 36, wherein the κ opioid receptors are located in the central nervous system.

38. A method according to claim 36, wherein the κ opioid receptors are located peripherally to the central nervous system.

39. A method according to claim 32, wherein the compound binds δ opioid receptors.

40. A method according to claim 39, wherein the δ opioid receptors are located in the central nervous system.

41. A method according to claim 39, wherein the δ opioid receptors are located peripherally to the central nervous system.

42. A method according to claim 32, wherein the binding antagonizes the activity of the opioid receptors.

43. A method according to claim 32, wherein the compound exhibits activity toward the opioid receptors.

44. A method according to claim 32, wherein the compound does not substantially cross the blood-brain barrier.

45. A method according to claim 32, which is for the prevention or treatment of a disease or condition selected from the group consisting of a condition or disease caused by an opioid, gastrointestinal dysfunction, ileus, obesity, and pain.

46. A method according to claim 45, wherein the condition or disease is caused by an opioid.

47. A method according to claim 46, wherein the opioid is endogenous.

48. A method according to claim 46, wherein the opioid is exogenous.

49. A method according to claim 32, wherein the composition further comprises an effective amount of at least one opioid.

50. A method according to claim 45, wherein the disease or condition is gastrointestinal dysfunction.

51. A method according to claim 45, wherein the disease or condition is ileus.

52. A method of claim 51, wherein the ileus is post-operative ileus.

53. A method according to claim 45, wherein the disease or condition is obesity.

54. A method according to claim 46, wherein the disease or condition is a side effect associated with an opioid.

55. A method according to claim 54, wherein the side effect is selected from the group consisting of constipation, nausea, vomiting, and combinations thereof.

56. A method according to claim 54, wherein the administering step occurs before, during or after a step of administering at least one opioid.

57. A method according to claim 56, wherein the opioid is alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol or mixtures thereof.

58. A method according to claim 45, wherein the disease or condition is pain.

59. A method according to claim 58, wherein the opioid is alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol or mixtures thereof.

60. A compound according to claim 28 which is 2-benzyl-3-[4a-(3-hydroxy-phenyl)-10a-methyl-3,4,4a,5,10,10a-hexahydro-1H-benzo[g]isoquinolin-2-yl]-propionic acid or a stereoisomer thereof.

61. A compound according to claim 28 which is {2-benzyl-3-[4a-(3-hydroxy-phenyl)-10a-methyl-3,4,4a,5,10,10a-hexahydro-1H-benzo[g]isoquinolin-2-yl]-propionylamino}-acetic acid or a stereoisomer thereof.

62. A compound according to claim 28 which is 3-(10a-methyl-2-phenethyl-1,3,4,5,10,10a-hexahydro-2H-benzo[g]isoquinolin-4a-yl)-benzamide or a stereoisomer thereof.

* * * * *